(12) United States Patent
Kurita et al.

(10) Patent No.: US 11,759,180 B2
(45) Date of Patent: Sep. 19, 2023

(54) MEDICAL SYSTEM AND MEDICAL INFORMATION TRANSFER METHOD

(71) Applicants: CANON MEDICAL SYSTEMS CORPORATION, Otawara (JP); Canon Kabushiki Kaisha, Ohta-ku (JP)

(72) Inventors: Koichiro Kurita, Otawara (JP); Hiroyuki Torikai, Meguro-ku (JP)

(73) Assignees: CANON MEDICAL SYSTEMS CORPORATION, Otawara (JP); Canon Kabushiki Kaisha, Ohta-ku (JP)

( * ) Notice: Subject to any disclaimer, the term of this patent is extended or adjusted under 35 U.S.C. 154(b) by 1118 days.

(21) Appl. No.: 16/426,467

(22) Filed: May 30, 2019

(65) Prior Publication Data
US 2019/0365356 A1    Dec. 5, 2019

(30) Foreign Application Priority Data

May 30, 2018  (JP) ................................ 2018-103084
May 28, 2019  (JP) ................................ 2019-099058

(51) Int. Cl.
*G16H 10/60*   (2018.01)
*A61B 8/08*    (2006.01)
(Continued)

(52) U.S. Cl.
CPC .......... *A61B 8/5215* (2013.01); *A61B 8/0866* (2013.01); *A61B 8/56* (2013.01);
(Continued)

(58) Field of Classification Search
CPC ....... A61B 8/5215; A61B 8/0866; A61B 8/56; A61B 8/565; A61B 8/461; G16H 30/20;
(Continued)

(56) References Cited

U.S. PATENT DOCUMENTS

2005/0139680 A1* 6/2005 Anttila .................. H04W 12/06
                                                     235/462.46
2005/0215900 A1   9/2005 Kim
(Continued)

FOREIGN PATENT DOCUMENTS

JP    2005-261925    9/2005
JP    2006-55511     3/2006
(Continued)

OTHER PUBLICATIONS

Japanese Office Action dated Feb. 7, 2023, in Japanese Patent Application No. 2019-099058, therein, 4 pages.

*Primary Examiner* — Jonathan Ng
*Assistant Examiner* — Benjamin L. Hanks
(74) *Attorney, Agent, or Firm* — Oblon, McClelland, Maier & Neustadt, L.L.P.

(57) ABSTRACT

A medical system according to an embodiment includes a medical apparatus and a first terminal. The medical apparatus is configured to have medical information therein. The first terminal is configured to be communicably connected to the medical apparatus so as to be able to transmit and receive the medical information thereto and therefrom, to have a function of an access point, and to cause a display to display a first code containing identification information of the access point. The first terminal is configured to be communicably connected to a second terminal having read the first code so as to be able to transmit and receive medical information thereto and therefrom.

16 Claims, 9 Drawing Sheets

(51) Int. Cl.
| | |
|---|---|
| *G16H 30/40* | (2018.01) |
| *A61B 8/00* | (2006.01) |
| *H04L 9/40* | (2022.01) |
| *H04L 67/12* | (2022.01) |
| *H04W 12/06* | (2021.01) |
| *H04W 12/50* | (2021.01) |
| *H04W 12/73* | (2021.01) |
| *H04W 12/75* | (2021.01) |
| *H04W 12/77* | (2021.01) |
| *G16H 30/20* | (2018.01) |
| *G16H 15/00* | (2018.01) |

(52) U.S. Cl.
CPC ............ *A61B 8/565* (2013.01); *G16H 30/20* (2018.01); *G16H 30/40* (2018.01); *H04L 63/0838* (2013.01); *H04L 67/12* (2013.01); *H04W 12/068* (2021.01); *H04W 12/50* (2021.01); *H04W 12/73* (2021.01); *H04W 12/75* (2021.01); *H04W 12/77* (2021.01); *A61B 8/461* (2013.01); *G16H 10/60* (2018.01); *G16H 15/00* (2018.01)

(58) Field of Classification Search
CPC ........ G16H 30/40; G16H 15/00; G16H 10/60; H04L 63/0838; H04L 67/12; H04W 12/068; H04W 12/50; H04W 12/73; H04W 12/75; H04W 12/77
See application file for complete search history.

(56) References Cited

U.S. PATENT DOCUMENTS

| | | | |
|---|---|---|---|
| 2007/0120955 A1 | 5/2007 | Shimosato | |
| 2013/0184587 A1* | 7/2013 | Eom | A61B 8/565 |
| | | | 600/443 |
| 2015/0065867 A1* | 3/2015 | Cho | A61B 8/464 |
| | | | 600/424 |
| 2016/0278739 A1 | 9/2016 | Pelissier et al. | |
| 2017/0065361 A1* | 3/2017 | Kurita | A61B 5/026 |
| 2017/0140120 A1* | 5/2017 | Thrower | G16H 40/67 |
| 2017/0325782 A1 | 11/2017 | Pelissier et al. | |
| 2017/0347056 A1 | 11/2017 | Kurita | |
| 2019/0090848 A1 | 3/2019 | Pelissier et al. | |
| 2019/0201138 A1* | 7/2019 | Yates | G16H 40/60 |

FOREIGN PATENT DOCUMENTS

| | | |
|---|---|---|
| JP | 2007-166577 | 6/2007 |
| JP | 2014-54366 | 3/2014 |
| JP | 56-08830 B1 | 10/2014 |
| JP | 2015-19729 | 2/2015 |
| JP | 2016-206716 A | 12/2016 |
| JP | 2016-209315 A | 12/2016 |
| JP | 6059789 B1 | 1/2017 |
| JP | 2017-51610 | 3/2017 |
| JP | 2017-209339 | 11/2017 |
| JP | 2018-509269 | 4/2018 |

\* cited by examiner

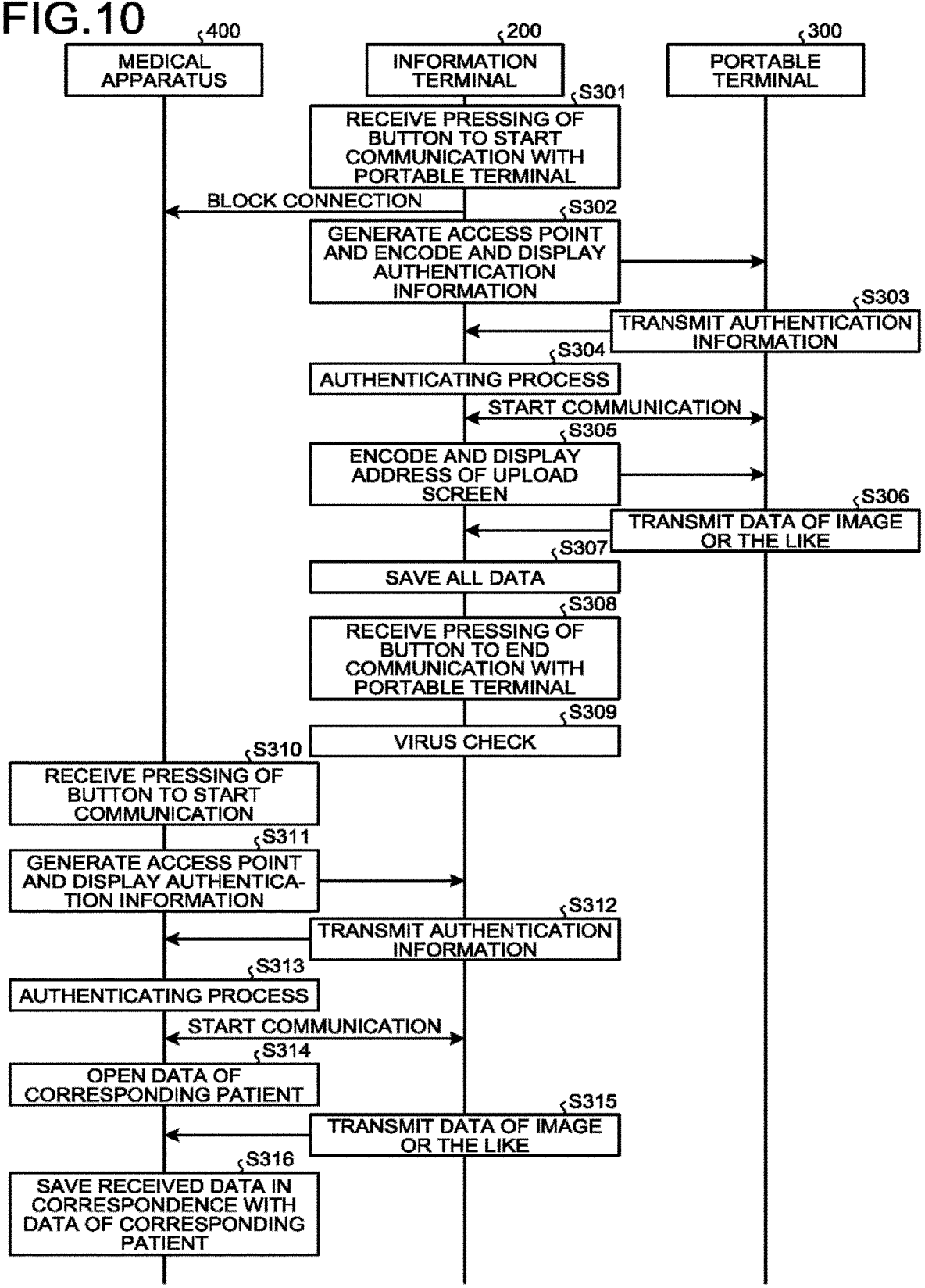

MEDICAL SYSTEM AND MEDICAL INFORMATION TRANSFER METHOD

CROSS-REFERENCE TO RELATED APPLICATIONS

This application is based upon and claims the benefit of priority from Japanese Patent Application No. 2018-103084, filed on May 30, 2018 and Japanese Patent Application No. 2019-99058, Filed on May 28, 2019; the entire contents of which are incorporated herein by reference.

FIELD

Embodiments described here relate generally to a medical system and a medical information transfer method.

BACKGROUND

While an ultrasound diagnosis apparatus and an information terminal are connected to each other by wireless communication, a function is conventionally known by which the ultrasound diagnosis apparatus can be manipulated and ultrasound images can be viewed through the information terminal in a real-time manner. This function may be called a second console. For example, this function can be used when it is difficult to manipulate the console and to view ultrasound images on the ultrasound diagnosis apparatus while a scan is performed with an ultrasound probe during a medical examination on a leg, for example, in which an ultrasound probe is brought into contact with the leg of a subject who is in a sitting position.

Further, another technique is also known by which an ultrasound diagnosis apparatus and a portable terminal owned by a subject are connected to each other by near field wireless communication, so as to transfer an ultrasound image from the ultrasound diagnosis apparatus to the portable terminal. This technique may be used, for example, when an ultrasound image of a fetus from an obstetric checkup is provided for the mother.

BRIEF DESCRIPTION OF THE DRAWINGS

FIG. 10 is a sequence chart illustrating a flow in a process performed in the ultrasound diagnosis system according to the second embodiment.

DETAILED DESCRIPTION

A medical system according to an embodiment includes a medical apparatus and a first terminal. The medical apparatus is configured to have medical information therein. The first terminal is configured to be communicably connected to the medical apparatus so as to be able to transmit and receive the medical information thereto and therefrom, to have a function of an access point, and to cause a display to display a first code containing identification information of the access point. The first terminal is configured to be communicably connected to a second terminal having read the first code so as to be able to transmit and receive medical information thereto and therefrom.

Exemplary embodiments of a medical system and a medical information transfer method will be explained below, with reference to the accompanying drawings. The embodiments described below are merely examples, and possible embodiments of the medical system and the medical information transfer method of the present disclosure are not limited to the examples explained below. Further, in the embodiments below, an ultrasound diagnosis system including an ultrasound diagnosis apparatus will be explained as an example of the medical system.

First Embodiment

Figure 1:
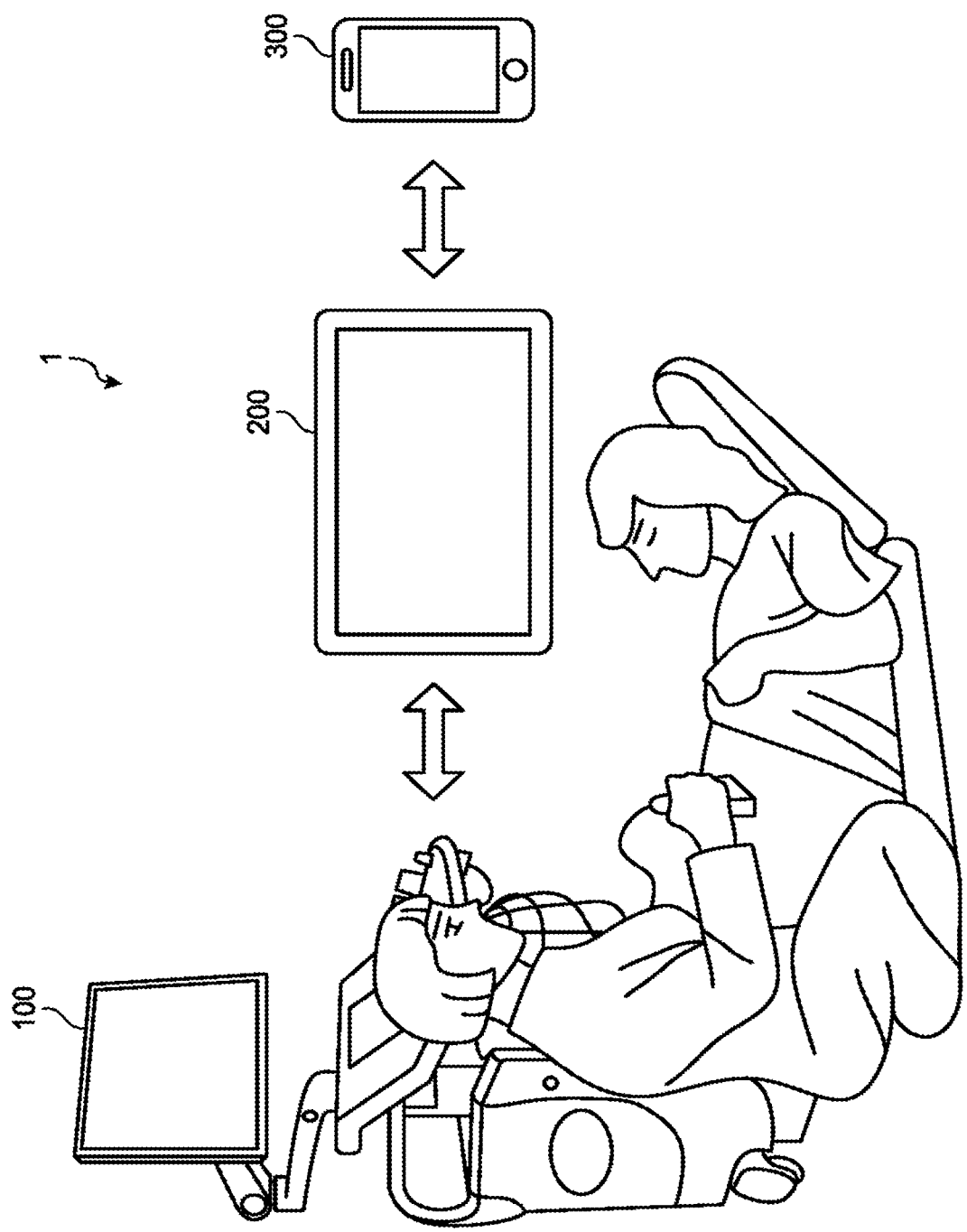
FIG. 1 is a drawing for explaining an overview of an ultrasound diagnosis system according to a first embodiment.

First, an overview of an ultrasound diagnosis system according to the present embodiment will be explained. FIG. 1 is a drawing for explaining an overview of an ultrasound diagnosis system 1 according to the first embodiment. FIG. 1 illustrates an example in which the ultrasound diagnosis system 1 according to the present embodiment is applied to an obstetric checkup. However, the ultrasound diagnosis system 1 according to the present embodiment is applicable not only to obstetric checkups, but also to other various situations.

As illustrated in FIG. 1, the ultrasound diagnosis system 1 includes an ultrasound diagnosis apparatus 100 and an information terminal 200, while the information terminal 200 is communicably connected to a portable terminal 300. The ultrasound diagnosis apparatus 100 includes an ultrasound probe, an input interface, a display, and an apparatus main body (a console) and is communicably connected to a network such as an intra-hospital Local Area Network (LAN). Further, the ultrasound diagnosis apparatus 100 is communicably connected to the information terminal 200 via a communication line different from the intra-hospital LAN. The communication connections of the ultrasound diagnosis apparatus 100 to the intra-hospital LAN and to the information terminal 200 may be wired or wireless.

The ultrasound diagnosis apparatus 100 is configured to generate an ultrasound image on the basis of ultrasound waves transmitted and received by the ultrasound probe as a result of an operator operating the ultrasound probe and to display the generated ultrasound image on the display. For example, as illustrated in FIG. 1, the ultrasound diagnosis apparatus 100 is used in an obstetric checkup and generates and displays an ultrasound image of a fetus. Further, the ultrasound diagnosis apparatus 100 is configured to transmit image data of an ultrasound image or the like to the information terminal 200, via the communication line different from the intra-hospital LAN.

The information terminal 200 is communicably connected to the ultrasound diagnosis apparatus 100 via the communication line different from the intra-hospital LAN and is configured to transmit and receive medical information. For example, the information terminal 200 receives the image data of the ultrasound image or the like from the ultrasound diagnosis apparatus and stores therein the received image data. The information terminal 200 may be, for example, Personal Computer (PC), a tablet PC, or the like. In this situation, when a second console function is applied to the ultrasound diagnosis system 1, the information terminal 200 is able to receive a manipulation to control the ultrasound diagnosis apparatus 100, to cause an ultrasound image to be acquired, and to arrange the acquired ultrasound image to be displayed.

For example, similarly to the input interface of the ultrasound diagnosis apparatus 100, the information terminal 200 is configured to receive various types of input operations to control the apparatus main body of the ultrasound diagnosis apparatus 100 and to control the apparatus main body of the ultrasound diagnosis apparatus 100 to acquire the ultrasound image. Further, the information terminal 200 is configured to receive the ultrasound image acquired by the ultrasound diagnosis apparatus 100 and to arrange the received ultrasound image to be displayed on a display thereof or to store the received ultrasound image into a memory.

In this situation, for example, the information terminal 200 is usable in a position away from the ultrasound diagnosis apparatus 100, as a result of being communicably connected to the ultrasound diagnosis apparatus 100 via wireless communication. Accordingly, an operator is able to manipulate the ultrasound diagnosis apparatus while viewing the ultrasound image displayed on the information terminal 200, even in a position where it is difficult to manipulate the console and to view the ultrasound image on the ultrasound diagnosis apparatus 100. For example, as illustrated in FIG. 1, it is possible to cause the ultrasound diagnosis apparatus 100 to acquire an ultrasound image of the abdomen of an examined subject (hereinafter, "subject"), by operating the information terminal 200 while scanning the abdomen of the lying subject with the ultrasound probe.

Further, the information terminal 200 is communicably connected to the portable terminal 300 via a communication line different from the communication line used for the communication connection to the ultrasound diagnosis apparatus 100 and is configured to transmit and receive various types of information to and from the portable terminal 300. For example, the information terminal 200 transmits image data of an ultrasound image or the like to the portable terminal 300. Further, for example, the information terminal 200 receives medical information such as a medical report from the portable terminal 300 and stores the received medical information therein. Further, the information terminal 200 transmits the medical information to a medical apparatus. The communication between the information terminal 200 and the portable terminal 300 will be explained in detail later.

The portable terminal 300 is communicably connected to the information terminal 200 and is configured to receive the ultrasound image. For example, the portable terminal 300 may be a Personal Digital Assistant (PDA), a tablet PC, a smartphone, or the like owned by the subject. In one example, the portable terminal 300 is a smartphone owned by the subject undergoing an obstetric checkup and is configured to receive the image data of the ultrasound image or the like of the fetus from the information terminal 200. In this situation, for example, the portable terminal 300 may be a device that is not capable of transmitting and receiving image data by near field wireless communication such as Bluetooth (registered trademark). In that situation, the portable terminal 300 may be a device having iOS (registered trademark) installed as an Operating System (OS) thereof, for example.

As explained above, in the ultrasound diagnosis system 1, the medical information such as the ultrasound image is transmitted and received between the ultrasound diagnosis apparatus 100 and the information terminal 200, and the medical information such as the ultrasound image is transmitted to the portable terminal 300 via the information terminal 200. In this situation, when the ultrasound image is to be transferred to the portable terminal 300 that is not capable of receiving image data via near field wireless communication, the portable terminal 300, in the current situation, becomes able to receive the image data when a dedicated application is installed therein. However, having to install the application to receive the image data causes trouble, and also downloading the application involves a cost (a communication fee).

To cope with this situation, the ultrasound diagnosis system 1 according to the first embodiment makes it possible to conveniently provide the portable terminal 300 owned by the subject with image data, by making it possible to receive the image data without the need to install the dedicated application. Further, the ultrasound diagnosis system 1 is also able to eliminate the burden of the communication fee, because there is no need to download the application. Further, the ultrasound diagnosis system 1 according to the first embodiment is able to avoid the situation where the portable terminal 300 owned by the subject is connected to the ultrasound diagnosis apparatus 100 or to the intra-hospital LAN via the information terminal 200, because when the information terminal 200 is communicably connected to the portable terminal 300, the communication connection to the ultrasound diagnosis apparatus 100 is blocked. With these arrangements, the ultrasound diagnosis system 1 also makes it possible to provide the portable terminal 300 with the image data in a secure manner.

Figure 2:
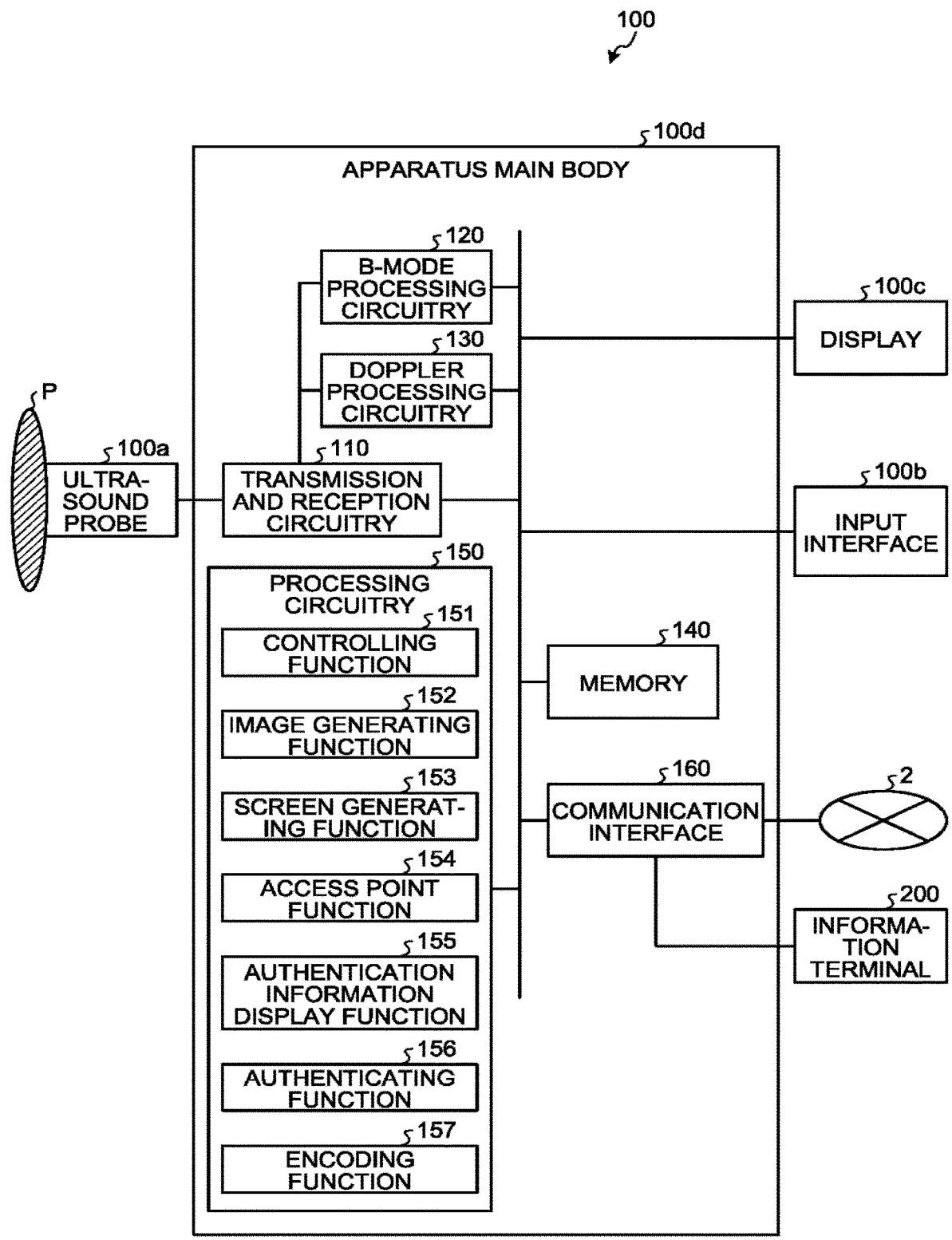
FIG. 2 is a block diagram illustrating an exemplary configuration of an ultrasound diagnosis apparatus according to the first embodiment.

In the following sections, details of the apparatuses in the ultrasound diagnosis system 1 will be explained. In the following sections, an example will be explained in which a second console is applied to the ultrasound diagnosis system 1. FIG. 2 is a block diagram illustrating an exemplary configuration of the ultrasound diagnosis apparatus 100 according to the first embodiment. As illustrated in FIG. 2, the ultrasound diagnosis apparatus 100 according to the first embodiment includes an ultrasound probe 100a, an input interface 100b, a display 100c, and an apparatus main body 100d. The ultrasound probe 100a, the input interface 100b, and the display 100c are communicably connected to the apparatus main body 100d.

The ultrasound probe 100a includes a plurality of piezoelectric transducer elements. Each of the plurality of piezoelectric transducer elements is configured to generate an ultrasound wave on the basis of a drive signal supplied thereto from transmission and reception circuitry 110 included in the apparatus main body 100d. Further, the ultrasound probe 100a is configured to receive reflected waves from a subject P and to convert the received reflected waves into electrical signals. In other words, the ultrasound probe 100a is configured to perform an ultrasound scan on the subject P and to receive the reflected waves from the subject P. Further, the ultrasound probe 100a includes a matching layer provided for the piezoelectric transducer elements, as well as a backing member or the like that prevents the ultrasound waves from propagating rearward from the piezoelectric transducer elements. In this situation, the ultrasound probe 100a is detachably connected to the apparatus main body 100d.

When an ultrasound wave is transmitted from the ultrasound probe 100a to the subject P, the transmitted ultrasound wave is repeatedly reflected on a surface of discontinuity of acoustic impedances at a tissue in the body of the subject P and is received as a reflected-wave signal by each of the plurality of piezoelectric transducer elements included in the ultrasound probe 100a. The amplitude of the received reflected-wave signal is dependent on the difference between the acoustic impedances the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The present embodiment is applicable to situations where the ultrasound probe 100a is a one-dimensional (1D) array probe configured to scan the subject two-dimensionally or is a three-dimensional probe configured to scan the subject three-dimensionally, i.e., a mechanical four-dimensional (4D) probe or a two-dimensional (2D) array probe.

The input interface 100b is realized by using a trackball, a switch button, a mouse, a keyboard, a touchpad used for performing an input operation by touching an operation surface thereof, a touch monitor in which a display screen and a touchpad are integrally formed, a contactless input circuit using an optical sensor, an audio input circuit, and/or the like used for setting a predetermined position (e.g., a region of interest) or the like. The input interface 100b is connected to processing circuitry 150 (explained later) and is configured to convert an input operation received from the operator into an electrical signal and to output the electrical signal to the processing circuitry 150. Further, the input interface 100b of the present disclosure does not necessarily have to include one or more physical operation component parts such as a mouse and a keyboard. For instance, possible examples of the input interface include an electrical signal processing circuit configured to receive an electrical signal corresponding to an input operation from an external input device provided separately from the apparatus and to output the electrical signal to the processing circuitry 150.

The display 100c is configured to display a Graphical User Interface (GUI) used by the operator of the ultrasound diagnosis apparatus 100 for inputting various types of setting requests via the input interface 100b and to display the ultrasound image generated by the apparatus main body 100d and the like. Further, the display 100c is configured to display various types of messages and display information to notify the operator of processing statuses and processing results of the apparatus main body 100d. Further, the display 100c includes a speaker and is also capable of outputting audio.

The apparatus main body 100d is an apparatus configured to generate the ultrasound image data on the basis of the reflected-wave signals received by the ultrasound probe 100a. For example, the apparatus main body 100d generates two-dimensional ultrasound image data on the basis of two-dimensional reflected-wave data (echo data) received by the ultrasound probe 100a. Further, the apparatus main body 100d also generates three-dimensional ultrasound image data (volume data) on the basis of three-dimensional reflected-wave data received by the ultrasound probe 100a. Further, the apparatus main body 100d generates a display-purpose ultrasound image from the generated ultrasound image data.

For example, as illustrated in FIG. 2, the apparatus main body 100d includes the transmission and reception circuitry 110, B-mode processing circuitry 120, Doppler processing circuitry 130, a memory 140, the processing circuitry 150, and a communication interface 160. The transmission and reception circuitry 110, the B-mode processing circuitry 120, the Doppler processing circuitry 130, the memory 140, the processing circuitry 150, and the communication interface 160 are connected so as to be able to communicate with one another. Further, the apparatus main body 100d is connected to a network 2. The network 2 is the intra-hospital LAN or the like, and the ultrasound diagnosis apparatus 100 is communicably connected to various types of apparatuses connected to the intra-hospital LAN via the network 2.

The transmission and reception circuitry 110 includes a pulse generator, a transmission delay unit, a pulser, and the like and is configured to supply the drive signal to the ultrasound probe 100a. The pulse generator is configured to repeatedly generate a rate pulse used for forming transmission ultrasound wave at a predetermined rate frequency. Further, the transmission delay unit is configured to apply a delay period that is required to converge the ultrasound waves generated by the ultrasound probe 100a into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 100a with timing based on the rate pulses. In other words, by varying the delay periods applied to the rate pulses, the transmission delay unit is able to arbitrarily adjust the transmission directions of the ultrasound waves transmitted from the surfaces of the piezoelectric transducer elements.

In this situation, the transmission and reception circuitry 110 has a function that is able to instantly change the transmission frequency, the transmission drive voltage, and the like, for the purpose of executing a predetermined scan sequence on the basis of an instruction from the processing circuitry 150 (explained later). In particular, the function to change the transmission drive voltage is realized by using a linear-amplifier-type transmission circuit of which the value can be instantly switched or by using a mechanism configured to electrically switch between a plurality of power source units.

Further, the transmission and reception circuitry 110 includes a pre-amplifier, an Analog/Digital (A/D) converter, a reception delay unit, an adder, and the like and is configured to generate reflected-wave data by performing various types of processes on the reflected-wave signals received by the ultrasound probe 100a. The pre-amplifier is configured to amplify the reflected-wave signals for each of the channels. The A/D converter is configured to perform an A/D conversion process on the amplified reflected-wave signals. The reception delay unit is configured to apply a delay period required to determine reception directionality, to the result of the A/D conversion. The adder is configured to generate the reflected-wave data by performing an adding process on the reflected-wave signals processed by the reception delay unit. As a result of the adding process performed by the adder, reflected components from the direction corresponding to the reception directionality of the reflected-wave signals are emphasized, so that a comprehensive beam used in the ultrasound transmission and reception is formed on the basis of the reception directionality and the transmission directionality.

When the subject P is to be two-dimensionally scanned, the transmission and reception circuitry 110 is configured to cause a two-dimensional ultrasound beam to be transmitted from the ultrasound probe 100a. Further, the transmission and reception circuitry 110 is configured to generate two-dimensional reflected-wave data from two-dimensional reflected-wave signals received by the ultrasound probe 100a. In contrast, when the subject P is to be three-dimensionally scanned, the transmission and reception circuitry 110 is configured to cause a three-dimensional ultrasound beam to be transmitted from the ultrasound probe 100a. Further, the transmission and reception circuitry 110 is configured to generate three-dimensional reflected-wave data from three-dimensional reflected-wave signals received by the ultrasound probe 100a.

In this situation, the output signal from the transmission and reception circuitry 110 may be in a form selected from among various forms such as being a signal called a Radio Frequency (RF) signal including phase information or being amplitude information obtained after an envelope detecting process.

The B-mode processing circuitry 120 is configured to receive the reflected-wave data from the transmission and reception circuitry 110 and to generate data (B-mode data) in which signal intensities are expressed with levels of brightness, by performing a logarithmic amplification process, an envelope detecting process, and/or the like thereon.

The Doppler processing circuitry 130 is configured to generate data (Doppler data) obtained by extracting moving member information such as velocity, dispersion, power, and the like with respect to multiple points, by performing a frequency analysis to obtain velocity information from the reflected-wave data received from the transmission and reception circuitry 110 and extracting a blood flow, a tissue, and a contrast agent echo component influenced by the Doppler effect. More specifically, as motion information of the moving members, the Doppler processing circuitry 130 generates Doppler data at each of a plurality of sampling points, with an average velocity value, an average dispersion value, an average power value, or the like. In this situation, the moving members may be, for example, a blood flow, a tissue such as a cardiac wall, and a contrast agent. As the motion information of the blood flow (blood flow information), the Doppler processing circuitry 130 generates information obtained by estimating, at each of the plurality of sampling points, an average velocity value of the blood flow, an average dispersion value of the blood flow, an average power value of the blood flow, and the like.

The Doppler processing circuitry 130 includes a Moving Target indicator (MTI) filter and a blood flow, information generating unit and is configured, for example, to implement a color Doppler method and to calculate the blood flow information. According to the color Doppler method, ultrasound transmission and reception is performed multiple times on the same scanning line, so as to extract signals derived from the blood flow, by suppressing signals (clutter signals) derived from stationary or slow-moving tissues by applying a Moving Target Indicator (MTI) filter to a data sequence from mutually the same position. Further, according to the color Doppler method, the blood flow information such as velocity of the blood flow, dispersion of the blood flow, power of the blood flow, and the like are estimated on the basis of the blood flow signals.

By using a filter matrix, the MTI filter is configured to output a data sequence in which clutter components are suppressed and the blood flow signals derived from the blood flow are extracted, on the basis of a data sequence made up of sequential pieces of reflected-wave data from mutually the same position (the same sampling points). The blood flow information generating unit is configured to perform a calculation such as an autocorrelation calculation by using the data output by the MTI filter, to estimate the blood flow information, and to output the estimated blood flow information as Doppler data. As the MTI filter, it is possible to use, for example, a Butterworth Infinite Impulse Response (IIR) filter, a filter having a fixed coefficient such as a polynomial regression filter, an adaptive filter that varies coefficients in accordance with an input signal by using an eigenvector, or the like.

The B-mode processing circuitry 120 and the Doppler processing circuitry 130 illustrated in FIG. 2 are capable of processing both the two-dimensional reflected-wave data and the three-dimensional reflected-wave data. In other words, the B-mode processing circuitry 120 is configured to generate two-dimensional B-mode data from the two-dimensional reflected-wave data and to generate three-dimensional ode data from the three-dimensional reflected-wave data. Further, the Doppler processing circuitry 130 is configured to generate two-dimensional Doppler data from the two-dimensional reflected-wave data and to generate three-dimensional Doppler data from the three-dimensional reflected-wave data.

The memory 140 is configured to store therein control programs for performing ultrasound transmissions and receptions, image processing processes, and display processes as well as various types of data such as diagnosis information (e.g., patients' IDs, medical doctors' observations), diagnosis protocols, various types of body marks, and the like. Further, the memory 140 is configured to store therein various types of image data. For example, the memory 140 also stores therein any of the data generated by the B-mode processing circuitry 120 and the Doppler processing circuitry 130. The operator is able to invoke any of the B-mode data and the Doppler data stored in the memory 140 after a diagnosing process, for example. The invoked B-mode data and Doppler data can serve as the display-purpose ultrasound images after being routed through the processing circuitry 150. Further, the memory 140 is also capable of storing the reflected-wave data therein. In addition, the memory 140 stores therein screen data transmitted from the ultrasound diagnosis apparatus 100 to the information terminal 200. The screen data will be explained in detail later. For example, the memory 140 is realized by using, for example, a semiconductor memory element such as a Random Access Memory (RAM) or a flash memory, or a hard disk or an optical disk.

It is possible to transfer any of the data stored in the memory 140 to an external apparatus via the network 2. The external apparatus may be, for example, a Personal Computer (PC) used by a medical doctor who performs an image diagnosis process, a storage medium such as a Compact Disk (CD), a Digital Versatile Disk (DVD), a printer, or the like. Further, it is possible to transfer any of the data stored in the memory 140 to the information terminal 200 via a communication line different from the network 2. As for the mode of storage into the memory 140, the memory 140 may temporarily save live information therein and may save data therein for long-term recording purposes.

The processing circuitry 150 is configured to control overall processes performed by the ultrasound diagnosis apparatus 100. More specifically, on the basis of the various types of setting requests input from the operator via the input interface 100b and various types of control programs and various types of data read from the memory 140, the processing circuitry 150 controls processes performed by the transmission and reception circuitry 110, the B-mode processing circuitry 120, and the Doppler processing circuitry 130. Further, the processing circuitry 150 exercises control so that any of the display-purpose ultrasound images stored in the memory 140 is displayed on the display 100c, the touch monitor of the input interface 100b, or the like. Further, in response to a request input from the operator via the information terminal 200, the processing circuitry 150 controls processes performed by the circuits described above.

The processing circuitry 150 executes a controlling function 151, an image generating function 152, a screen generating function 153, an access point function 154, an authentication information display function 155, an authenticating function 156, and an encoding function 157.

In this situation, for example, the processing functions executed by the constituent elements of the processing circuitry 150, namely, the controlling function 151, the image generating function 152, the screen generating function 153, the access point function 154, the authentication information display function 155, the authenticating function 156, and the encoding function 157 are stored in the memory 140 in the form of computer-executable programs. The processing circuitry 150 is a processor configured to realize the functions corresponding to the programs by reading and executing the programs from the memory 140. In other words, the processing circuitry 150 that has read the programs has the functions indicated in the processing circuitry 150.

The communication interface 160 is an interface used for communicating with the various types of apparatuses connected to the intra-hospital LAN via the network 2. Further, the communication interface 160 is an interface used for communicating with the information terminal 200 via the communication line different from the network 2. Through the communication interface 160, the processing circuitry 150 communicates with the apparatuses connected to the intra-hospital LAN and communicates with the information terminal 200. For example, through the communication interface 160, the processing circuitry 150 is able to exchange various types of data with external apparatuses other than the ultrasound diagnosis apparatus 100.

The controlling function 151 is configured to control the entirety of the ultrasound diagnosis apparatus 100. For example, by controlling the transmission and reception circuitry 110, the B-mode processing circuitry 120, and the Doppler processing circuitry 132, the controlling function 151 controls the acquisition of the reflected-wave data and the generation of the B-mode data and the Doppler data. In other words, via the ultrasound probe 100a, the controlling function 151 causes two-dimensional ultrasound scans and three-dimensional ultrasound scans to be performed on the subject. Further, the controlling function 151 exercises control so that various types of processes such as a measuring process are performed and so that the display 100c displays processing results. Further, the controlling function 151 exercises control so that the display 100c displays ultrasound images and the like generated by the image generating function 152.

The image generating function 152 is configured to generate the ultrasound image data from the data generated by the B-mode processing circuitry 120 and the Doppler processing circuitry 130. In other words, the image generating function 152 is configured to generate two-dimensional B-mode image data in which intensities of the reflected waves are expressed with levels of brightness, from the two-dimensional B-mode data generated by the B-mode processing circuit 120. Further, the image generating function 152 is configured to generate two-dimensional Doppler image data expressing the moving member information, from the two-dimensional Doppler data generated by the Doppler processing circuitry 130. The two-dimensional Doppler image data may be a velocity image, a dispersion image, a power image, or an image combining any of these images. Further, the image generating function 152 is also capable of generating M-mode image data from time-series data of B-mode data on a scanning line generated by the B-mode processing circuitry 120. Further, the image generating function 152 is also capable of generating a Doppler waveform obtained by plotting pieces of velocity information of a blood flow or a tissue along a time series, from the Doppler data generated by the Doppler processing circuitry 130.

In this situation, generally speaking, the image generating function 152 converts (by performing a scan convert process) a scanning line signal sequence from an ultrasound scan into a scanning line signal sequence in a video format used by, for example, television and generates display-purpose ultrasound images. More specifically, the image generating function 152 generates the display-purpose ultrasound images by performing a coordinate transformation process compliant with the ultrasound scan mode used by the ultrasound probe 100a. Further, as various types of image processing processes besides the scan convert process, the image generating function 152 performs, for example, an image processing process (a smoothing process) to re-generate a brightness average value image, an image processing process (an edge enhancement process) that uses a differential filter inside an image, or the like, by using a plurality of image frames resulting from the scan convert process. Also, the image generating function 152 combines text information of various types of parameters, scale graduations, body marks, various types of markers, and the like with the ultrasound images.

In other words, the B-mode data and the Doppler data are each ultrasound image data before the scan convert process. The data generated by the image generating function 152 is the display-purpose ultrasound images after the scan convert process.

Further, the image generating function 152 is configured to generate three-dimensional B-mode image data by performing a coordinate transformation process on the three-dimensional B-mode data generated by the B-mode processing circuitry 120. Further, the image generating function 152 is configured to generate three-dimensional Doppler image data by performing a coordinate transformation process on the three-dimensional Doppler data generated by the Doppler processing circuitry 130. In other words, the image generating function 152 is configured to generate the "three-dimensional B-mode image data and three-dimensional Doppler image data" as "three-dimensional ultrasound image data (volume data)". Further, the image generating function 152 generates a Multi Planar Reconstruction (MPR) image by performing a multi-planar transformation on the three-dimensional B-mode image data or the three-dimensional Doppler image data, and also generates a volume rendering image by performing a volume rendering process on the three-dimensional B-mode image data or the three-dimensional Doppler image data.

The screen generating function 153 is configured to generate screen data to be transmitted to the information terminal 200. More specifically, the screen generating function 153 receives a command signal from the information terminal 200 via the communication interface 160, reads the screen data corresponding to the received command signal from the memory 140, and transmits the screen data to the information terminal 200.

In this situation, the screen data is, for example, image data of an operation screen generated to simulate an operation screen displayed on a touch panel included in the input interface 100b. In one example, the image data of the operation screen is image data indicating functional buttons used for receiving operations from the operator. Further, the screen data may be image data of one or more panel switches generated to simulate the shapes of the panel switches included in the input interface 100b. In one example, the image data of the panel switches is image data indicating at least one panel switch arranged on the front face of the ultrasound diagnosis apparatus 100.

In this situation, the screen data is kept in correspondence with additional information indicating what functions are executed by the functional buttons and the panel switches. In other words, the screen data is kept in correspondence with function information about the functions included in the screen data and with position information indicating the positions in which the functional buttons and the panel switches corresponding to such functions are arranged. The screen data is generated in advance and stored in the memory 140.

The screen generating function 153 is configured to read any of the screen data corresponding to the command signal received from the information terminal 200 and to transmit the read screen data to the information terminal 200. For example, the information terminal 200 is configured to transmit the command signal requesting screen data corresponding to an initial screen of the second console, an operation screen used for operating various types of functions, or a screen displaying an ultrasound image, to the ultrasound diagnosis apparatus 100. The screen generating function 153 transmits the screen data corresponding to the received command signal to the information terminal 200 via the communication interface 160. The information terminal 200 arranges the screen data received from the ultrasound diagnosis apparatus 100 to be displayed and receives an operation to cause the ultrasound diagnosis apparatus 100 to execute any of the various types of functions. The information terminal 200 causes the ultrasound diagnosis apparatus 100 to execute the function corresponding to a position in which an operation was received, by specifying the function corresponding to the position in which the operation was received on the basis of the additional information kept in correspondence with the screen data and transmitting a command signal corresponding to the specified function to the ultrasound diagnosis apparatus 100.

The access point function 154 is a software AP function configured to generate a virtual access point used by the information terminal 200 to communicate with the ultrasound diagnosis apparatus 100. More specifically, when a second console start button is pressed, the access point function 154 generates the virtual access point by controlling the communication interface 160. In this situation, the second console start button is, for example, provided in a predetermined position on the touch panel included in the input interface 100b. In one example, the second console start button may be provided as one of a plurality of switch buttons provided for the panel switches included in the input interface 100b.

In this situation, when generating the access point, the access point function 154 sets a Service Set Identifier (SSID) and a password. The SSID and the password may manually be set as a result of the operator inputting the information via the input interface 100b or may automatically be set. In this situation, the password is a one-time password that is updated either every time the ultrasound diagnosis apparatus 100 and the information terminal 200 are communicably connected to each other or regularly. The one-time password is, for example, a password generated on the basis of a mathematical algorithm, or the like.

Further, the access point function 154 is configured to be communicably connected to the information terminal 200 via the communication interface 160, on the basis of connection information that is set in advance. In this situation, in the present embodiment, an authenticating process related to the communication connection between the ultrasound diagnosis apparatus 100 and the information terminal 200 is automatically performed on the basis of the connection information set in advance. The connection information set in advance denotes information related to the communication connection such as the SSID of the generated access point, the password used for the connection, and Media Access Control (MAC) addresses of the ultrasound diagnosis apparatus 100 and the information terminal 200.

In one example, the access point function 154 may be configured to establish the communication connection after receiving a communication connection request from the information terminal 200. In that situation, the authenticating process related to the communication connection is performed by judging, on the ultrasound diagnosis apparatus 100, whether the password or the like input on the information terminal 200 is correct or not.

Further, after the communication connection to the information terminal 200 is established, the access point function 154 transmits, via the communication interface 160, a request to input a password used for allowing the ultrasound diagnosis apparatus 100 to be manipulated from the information terminal 200, to the information terminal 110.

The authentication information display function 155 is configured to present identification information used for manipulating the ultrasound diagnosis apparatus 100 through the information terminal 200. For example, the authentication information display function 155 displays, on the display 100c, the identification information including the SSID and the password set by the access point function 154. In this situation, the password included in the identification information is a string of made up of one of more characters, symbols, and/or numerals determined in advance to authenticate whether or not the operator is a legitimate user allowed to manipulate the ultrasound diagnosis apparatus 100 through the information terminal 200. Accordingly, the password may be different from the password set by the access point function 154. However, in that situation also, the password is a one-time password updated either every time the ultrasound diagnosis apparatus 100 and the information terminal 200 are communicably connected to each other or regularly. Although the example was explained in which the SSID and the password are used as the identification information, it is also acceptable to use an ID different from the SSID and a password as the identification information.

When response data is received from the information terminal 200 in response to the password input request transmitted from the access point function 154, the authenticating function 156 is configured to perform an authenticating process on the received response data. More specifically, the authenticating function 156 receives the response data sent from the information terminal 200 in response to the password input request, via the communication interface 160. Further, the authenticating function 156 compares the password included in the received response data with the password displayed by the authentication information display function 155. In this situation, when the password included in the response data matches the password displayed by the authentication information display function 155, the authenticating function 156 permits the operator to manipulate the ultrasound diagnosis apparatus 100 through the information terminal 200.

The encoding function 157 is configured to compress the ultrasound image generated by the image generating function 152 and the screen data obtained by the screen generating function 153 from the memory 140. For example, the encoding function 157 compresses the ultrasound image by using a compression technique such as a Joint Photographic Experts Group (JPEG) scheme. Further, for example, the encoding function 157 compresses the screen data including the additional information, by using a compression technique such as a Moving Picture Experts Group (MPEG) scheme.

The controlling function 151 transmits the ultrasound image and the screen data compressed by the encoding function 157 to the information terminal 200 via the communication interface 160. For example, the controlling function 151 transmits, to the information terminal 200, the screen data generated in response to the command signal transmitted by the information terminal 200 and subsequently compressed. Further, for example, the controlling function 151 transmits, to the information terminal 200, the ultrasound image acquired as a result of the operator operating the information terminal 200 and subsequently compressed.

Figure 3:
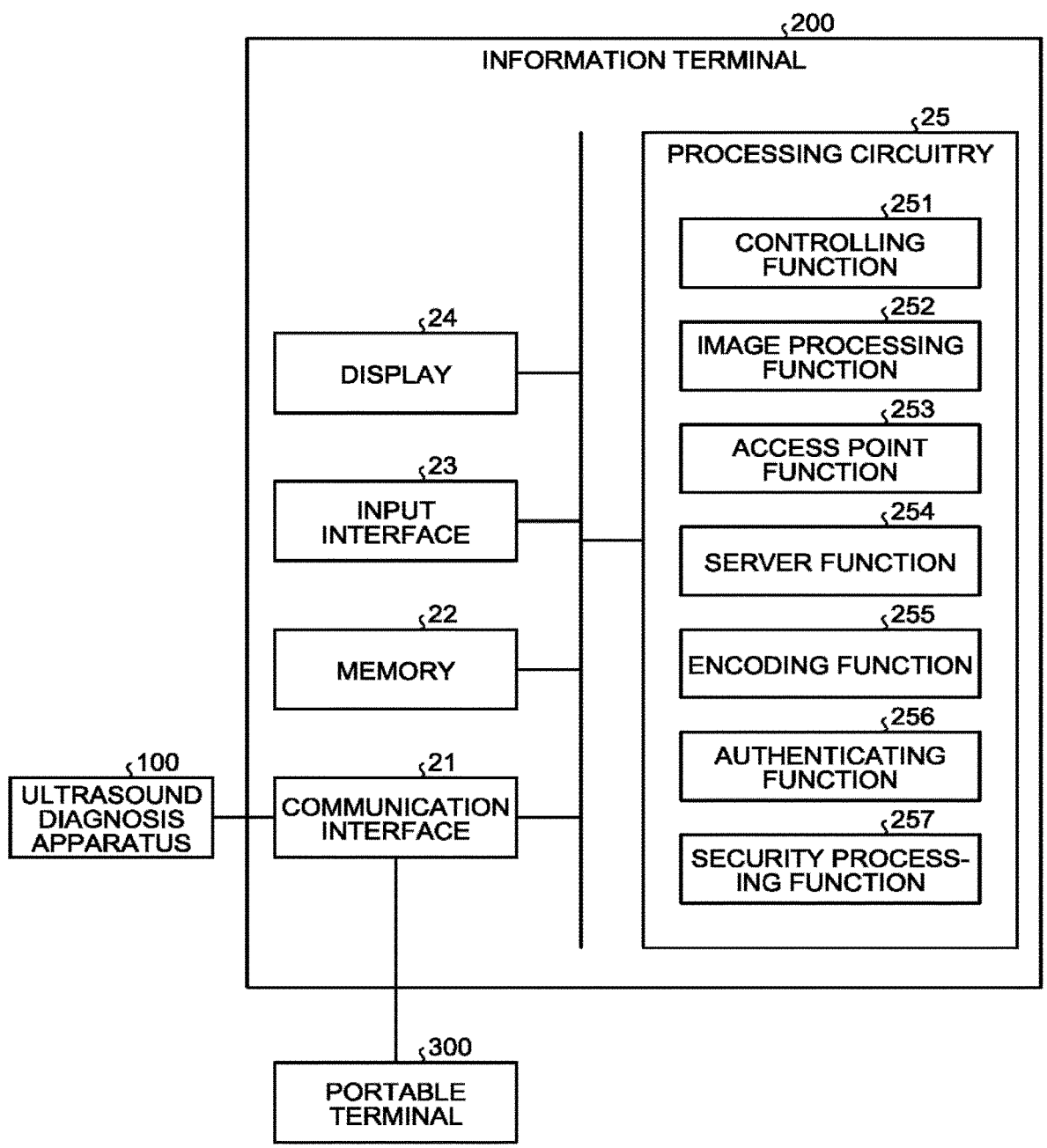
FIG. 3 is a block diagram illustrating an exemplary configuration of an information terminal according to the first embodiment.

FIG. 3 is a block diagram illustrating an exemplary configuration of the information terminal 200 according to the first embodiment. As illustrated in FIG. 3, the information terminal 200 includes a communication interface 21, a memory 22, an input interface 23, a display 24, and a processing circuitry 25. Further, the information terminal 200 is communicably connected to the ultrasound diagnosis apparatus 100 via the communication line different from the network 2. Further, the information terminal 200 is communicably connected to the portable terminal 300 via another communication line different from the communication line used for the communication connection to the ultrasound diagnosis apparatus 100.

The communication interface 21 is an interface used for communicating with the ultrasound diagnosis apparatus 100 via the communication line different from the network 2. Further, the communication interface 21 is an interface used for communicating with the portable terminal 300 via the other communication line different from the communication line to the ultrasound diagnosis apparatus 100. By using the communication interface 21, the processing circuitry 25 is configured to communicate with the ultrasound diagnosis apparatus 100 and to communicate with the portable terminal 300. For example, by using the communication interface 21, the processing circuitry 25 is capable of exchanging various types of data with the ultrasound diagnosis apparatus 100 and exchanging various types of data with the portable terminal 300.

The memory 22 is configured to store therein control programs used in various types f processes performed by the information terminal 200, various types of image data, and the like. For example, the memory 22 stores therein the ultrasound image and the screen data received from the ultrasound diagnosis apparatus 100. Further, for example, the memory 22 stores therein processing results obtained by the processing circuitry 25. For example, the memory 22 is realized by using a semiconductor memory element such as a Random Access Memory (RAM), a flash memory, or the like, or a hard disk or an optical disk.

It is possible to transfer any of the data stored in the memory 22 to an external apparatus via a communication line. For example, it is possible to transfer any of the data stored in the memory to the portable terminal 300 via a communication line different from the communication line to the ultrasound diagnosis apparatus 100. As for the mode of storage into the memory 22, the memory 22 may temporarily save live information therein and may save data therein for long-term recording purposes.

The input interface is realized by using a trackball, a switch button, a mouse, a keyboard, a touchpad used for performing an input operation by touching an operation surface thereof, a touch monitor in which a display screen and a touchpad are integrally formed, a contactless input circuit using an optical sensor, an audio input circuit, and/or the like used for performing input operations. The input interface 23 is connected to the processing circuitry 25 and is configured to convert an input operation received from the operator into an electrical signal and to output the electrical signal to the processing circuitry 25. The input interface 23 of the present disclosure does not necessarily have to include one or more physical operation component parts such as a mouse and a keyboard. For example, possible examples the input interface include an electrical signal processing circuit configured to receive an electrical signal corresponding to an input operation from an external input device provided separately from the apparatus and to output the electrical signal to the processing circuitry 25.

The display 24 is configured to display a Graphical User Interface (GUI) used by the operator of the information terminal 200 for inputting various types of requests via the input interface 23 and to display various types of messages and display information to notify the operator of processing results obtained by the processing circuitry 25, and the like. Further, the display 24 is configured to display the screen data and the ultrasound image received from the ultrasound diagnosis apparatus 100, and the like. For example, the display 24 may be a liquid crystal display device, an Organic Light Emitting Diode (OLED) display device, or the like. When the information terminal 200 is a tablet PC, the display 24 is integrally formed with the input interface 23. Further, the display 24 includes a speaker and is also capable of outputting audio.

The processing circuitry 25 is configured to control overall processes performed by the information terminal 200. More specifically, on the basis of the various types of setting requests input from the operator via the input interface 23 and various types of control programs and various types of data read from the memory 22, the processing circuitry 25 is configured to control various types of processes. For example, the processing circuitry 25 exercises control so that the display 24 displays any of the ultrasound images the like stored in the memory 22. Further, for example, the processing circuitry 25 establishes a communication connection to the portable terminal 300 and to transmit and receive various types of data to and from the portable terminal 300.

The processing circuitry 25 is configured to execute a controlling function 251, an image processing function 252, an access point function 253, a server function 254, an encoding function 255, an authenticating function 256, and a security processing function 257.

In this situation, for example, the processing functions executed by the constituent elements of the processing circuitry 25, namely, the controlling function 251, the image processing function 252, the access point function 253, the server function 254, the encoding function 255, the authenticating function 256, and the security processing function 257 are stored in the memory 22 in the form of computer-executable programs. The processing circuitry 25 is a processor configured to realize the functions corresponding to the programs by reading and executing the programs from the memory 22. In other words, the processing circuitry 25 that has read the programs has the functions indicated in the processing circuitry 25.

The controlling function 251 is configured to control the entirety of the information terminal 200. For example, the controlling function 251 controls transmissions and receptions of various types of data to and from the ultrasound diagnosis apparatus 100 via the communication interface 21. In one example, the controlling function 251 controls the transmission to the ultrasound diagnosis apparatus 100 of the identification information used for the authenticating process for manipulating the ultrasound diagnosis apparatus 100 through the information terminal 200 and the reception of the screen data and the ultrasound image from the ultrasound diagnosis apparatus 100.

Further, the controlling function 251 exercises control so that the display 24 displays the screen data and the ultrasound image received from the ultrasound diagnosis apparatus 100. Further, when an input operation is performed on any of the functional buttons and the panel switches included in the screen data, the controlling function 251 specifies the function corresponding to the operated functional button or panel switch, on the basis of the additional information. Further, the controlling function 251 exercises control so as to generate a command signal of the specified function and to transmit the generated command signal to the ultrasound diagnosis apparatus 100. Further, the controlling function 251 performs a process based on the response data received from the ultrasound diagnosis apparatus 100 in response to the command signal. In one example, when having transmitted a command signal to change the operation screen, the controlling function 251 exercises control so that the display 24 displays screen data received in response to the command signal.

Further, the controlling function 251 controls the transmission of the image data to the portable terminal 300. More specifically, the controlling function 251 control the transmission of the image data to the portable terminal 300 with which a communication connection has been established as a result of a process performed by other functions in the processing circuitry 25. Details of this control will be explained later.

As explained above, in the ultrasound diagnosis system 1 according to the first embodiment, the ultrasound diagnosis apparatus 100 and the information terminal 200 are communicably connected so as to transmit and receive the various types of data to and from each other. In this situation, because the second console is applied to the ultrasound diagnosis system 1, it is possible to manipulate the ultrasound diagnosis apparatus 100 through the information terminal 200.

Figure 4:
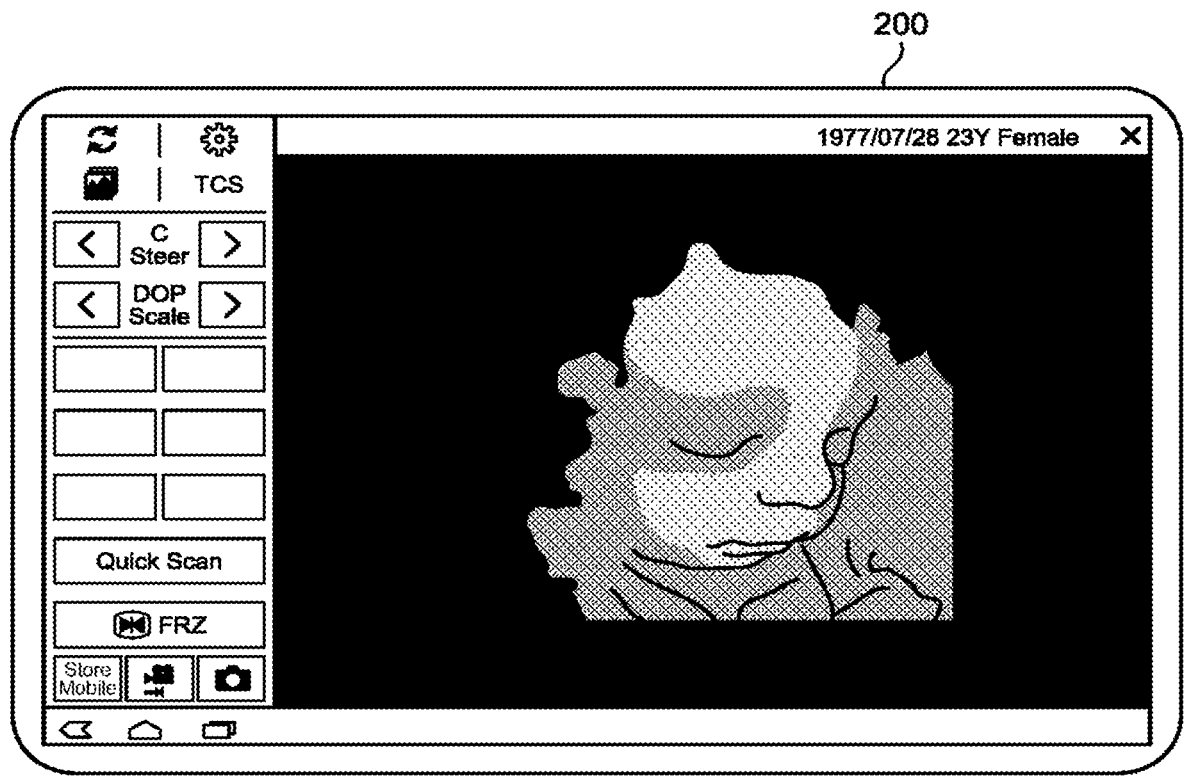
FIG. 4 is a drawing illustrating an example of a display on the information terminal according to the first embodiment.

For example, by causing the display 24 to display the screen data received after the communication connection is established with the ultrasound diagnosis apparatus 100, the information terminal 200 is able to display an operation screen on which various types of functional buttons are arranged as illustrated in FIG. 4. Further, by causing the display 24 to display the ultrasound image received from the ultrasound diagnosis apparatus 100, the information terminal 200 is able, for example, to display an ultrasound image of a fetus, as illustrated in FIG. 4. In this situation, when the second console is functioning in the ultrasound diagnosis system 1, an ultrasound image currently being acquired is transmitted to the information terminal 200 in a real-time manner. In other words, the operator is able to scan the abdomen of the subject with the ultrasound probe 100a, while viewing the acquired ultrasound image in a real-time manner on the display 24 of the information terminal 200. FIG. 4 is a drawing illustrating the example of the display on the information terminal 200 according to the first embodiment.

In this situation, in the ultrasound diagnosis system 1 according to the first embodiment, as a result of a process performed by the processing circuitry 25 included in the information terminal 200 explained in detail below, it is possible to conveniently provide the portable terminal 300 owned by the subject with image data handled within the ultrasound diagnosis system 1. More specifically, the ultrasound diagnosis system 1 makes it possible to conveniently provide the image data for the portable terminal 300 that is not capable of receiving the image data through near field wireless communication. In the following sections, details of a process performed by the processing circuitry 25 will be explained. In the following sections, the ultrasound image, the screen data, and the like that can be provided for the portable terminal 300 from the information terminal 200 will collectively be referred to as image data.

Returning to the description of FIG. 3, the image processing function 252 is configured to perform various types of image processing processes on the ultrasound image and the screen data received from the ultrasound diagnosis apparatus 100. For example, the image processing function 252 performs an image processing process to delete personal information included in the screen data or the ultrasound image to be transferred to the portable terminal 300. In one example, the image processing function 252 removes or blots out a region of the personal information included in the ultrasound image. In other words, the information terminal 200 exercises control so that the ultrasound image in an anonymised state is provided for the portable terminal 300.

In this situation, the image data to be transferred to the portable terminal 300 may be determined with any of various timing. For example, the transferred image data may be determined while a plurality of acquired ultrasound images are being displayed on the information terminal 200 when a series of medical examinations are finished or may be determined from among ultrasound images being displayed on the information terminal 200 in a real-time manner while the ultrasound probe 100a is performing a scan. When the ultrasound image to be transferred is determined from among the plurality of acquired ultrasound images when a series of medical examinations are finished, the transferred ultrasound image may be determined any time as long as it is before start button to start the transfer is pressed. In another example, when the transferred ultrasound image is determined from among the plurality of acquired ultrasound images when a series of medical examinations are finished, two or more of the ultrasound images may be selected as the ultrasound images to be transferred.

In this situation, the image processing function 252 is capable of performing not only the anonymization process of the image data, but also other image processing processes, as appropriate, such as enlarging/reducing image data and extracting a region of interest from the ultrasound image, for example.

The access point function 253 is a software AP function configured to generate a virtual access point used by the information terminal 200 to communicate with the portable terminal 300. More specifically, when a transfer button is pressed to transfer the image data to the portable terminal 300, the access point function 253 generates the virtual access point by controlling the communication interface 21. In this situation, for example, the transfer button is provided on the touch panel included in the input interface 23 and is pressed after the image data to be transferred to the portable terminal 300 is determined.

In this situation, when generating the access point, the access point function 253 sets an SSID and a password. The SSID and the password may manually be set as a result of the operator inputting the information via the input interface 23 or may automatically be set. In this situation, the password is a one-time password that is updated either every time the information terminal 200 and the portable terminal 300 are communicably connected to each other or regularly.

Further, when the communication connection of the portable terminal 300 to the information terminal 200 is permitted in the authenticating process performed by the authenticating function 256 (explained later), the access point function 253 establishes the communication connection between the information terminal 200 and the portable terminal 300. The authenticating process performed by the authenticating function 256 will be explained in detail later.

As explained above, when the information terminal 200 and the portable terminal 300 are communicably connected to each other, the communication connection between the information terminal 200 and the ultrasound diagnosis apparatus 100 is cut off in the ultrasound diagnosis system 1. In other words, the ultrasound diagnosis system 1 is configured so as to invalidate the communication connection between the information terminal 200 and the ultrasound diagnosis apparatus 100, before the information terminal 200 and the portable terminal 300 are communicably connected to each other. For example, when the transfer button is pressed, the controlling function 251 exercises control so as to cut off the communication connection established with the ultrasound diagnosis apparatus 100. With this arrangement, it is possible to avoid the situation where the portable terminal 300 owned by the subject is connected to the ultrasound diagnosis apparatus 100 or the intra-hospital LAN.

Figure 5:
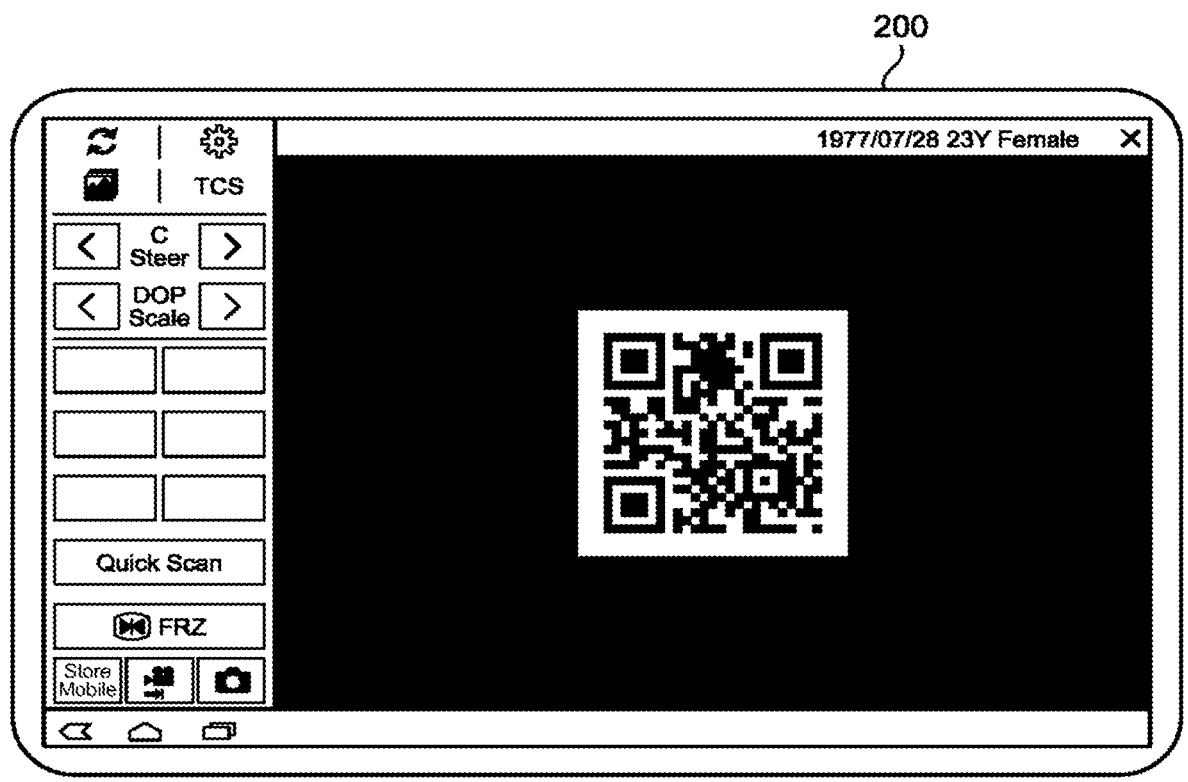
FIG. 5 is a drawing illustrating an example of a process performed by an encoding function according to the first embodiment.

The encoding function 255 is configured to encode various types of information. More specifically, the encoding function 255 is configured to encode information related to the transfer of the image data to the portable terminal 300, into a code that is decodable by the portable terminal 300. For example, as illustrated in FIG. 5, the encoding function 255 changes the SSID and the password set by the access point function 253 into a two-dimensional code. Further, for example, the encoding function 255 changes information about a storage location of the image data to be transferred to the portable terminal 300 into a two-dimensional code.

FIG. 5 is a drawing illustrating the example of the process performed by the encoding function 255 according to the first embodiment.

As explained above, when the transfer button to transfer the image data to the portable terminal 300 is pressed, in the information terminal 200 the access point function 253 is configured to generate the access point and to set the SSID and the password. Further, when the encoding function 255 has changed the SSID and the password set by the access point function 253 into the two-dimensional code, the controlling function 251 causes the display 24 to display the two-dimensional code.

The subject operates the portable terminal 300 of his/her own and reads the two-dimensional code displayed on the display 24 by using a camera. As a result, the portable terminal 300 obtains the SSID and the password for the virtual access point. When having obtained the SSID and the password, the portable terminal 300 makes the communication connection between the information terminal 200 and the portable terminal 300, by transmitting the obtained SSID and password, together with authentication information such as a MAC address of the portable terminal 300, to the information terminal 200. The transmission of the authentication information may automatically be performed in response to the two-dimensional code being read or may be performed as a result of the portable terminal 300 displaying a message indicating that a communication connection is to be made with the information terminal 200 so that the subject performs an operation to agree to making the communication connection to the information terminal 200.

The authenticating function 256 is configured to perform an authenticating process on the authentication information received from the portable terminal 300. More specifically, the authenticating function 256 receives the authentication information from the portable terminal 300 via the communication interface 21. Further, the authenticating function 256 compares the password included in the received authentication information with the password changed into the two-dimensional code. When the password included in the authentication information matches the password changed into the two-dimensional code, the authenticating function 256 permits the communication connection between the portable terminal 300 and the information terminal 200. In this situation, when the communication connection of the portable terminal 300 to the information terminal 200 is permitted, the access point function 253 establishes the communication connection between the information terminal 200 and the portable terminal 300.

In response to an image data browse request from the portable terminal 300, the server function 254 is configured to return a response. For example, the server function 254 is configured to function as a web server using Hypertext Transfer Protocol (HTTP) and to receive an HTTP request for browsing a Uniform Resource Locator (URL) of the storage location storing the image data from a web browser of the portable terminal 300. Further, in response to the received HTTP request, the server function 254 returns the image data to the web browser of the portable terminal 300.

In one example, when the transfer button is pressed, it is determined, at first, that data is to be transferred to the portable terminal 300, and the server function 254 stores image data on which image processing has been performed into a temporary storage region of the memory 22 and notifies the encoding function 255 of the URL of the storage location. In this situation, every time the transfer button is pressed, the server function 254 updates the URL each time, by changing the file name of the image data with the use of Globally Unique Identifier (GUID) of the image data or the time at which the image data was stored into the memory 22.

When being notified of the URL by the server function 254, the encoding function 255 changes the URL provided in the notification into a two-dimensional code. In this situation, the URL provided to the encoding function 255 is updated each time the transfer button is pressed. That is, the URL is encoded into a different code for each transfer by the encoding function 255. Further, when the URL has been changed into the two-dimensional code by the encoding function 255, the controlling function 251 causes the display 24 to display the two-dimensional code. In the example above, the example is explained in which the code changes for each transfer by updating the URL each time the transfer button is pressed; however, possible embodiments are not limited to those examples. For instance, the encoding function 255 can also change the code by encoding the provided URL by a different encoding method. In one example, the encoding function 255 changes the URL provided in the notification into a two-dimensional code in a different encoding method each time a communication connection between the information terminal 200 and the portable terminal 300 is established.

The subject operates the portable terminal 300 of his/her own and reads the two-dimensional code displayed on the display 24 by using the camera. As a result, the portable terminal 300 obtains the URL of the image data. When having obtained the URL of the image data, the portable terminal 300 transmits an HTTP request to browse the URL obtained by the web browser, to the information terminal 200. In response to the HTTP request received from the portable terminal 300, the server function 254 transfers the image data at the requested URL to the web browser of the portable terminal 300. In this situation, the web browser of the portable terminal 300 may automatically be activated in response to the two-dimensional code of the URL being read or may be activated as a result of the portable terminal 300 displaying a message indicating that the web browser is to be activated so that the subject performs an operation to agree to activating the web browser.

Figure 6:
FIG. 6 is a drawing illustrating an example of a display of an ultrasound image realized by a portable terminal according to the first embodiment.

Further, when the image data has been transferred thereto from the information terminal 200, the portable terminal 300 is able to have the ultrasound image of the fetus displayed in the web browser, as illustrated in FIG. 6, for example. In this situation, the subject is able to save the ultrasound image of the fetus in the portable terminal 300 of his/her own, by performing an operation to save the image data displayed in the web browser. In this situation, in the image data transferred to the portable terminal 300, as illustrated in FIG. 6, the personal information is anonymized as a result of the process performed by the image processing function 252. FIG. 6 is a drawing illustrating the example of the display of the ultrasound image realized by the portable terminal 300 according to the first embodiment.

As explained above, when the transfer of the image data to the portable terminal 300 is completed, the operator performs an operation to cut off the communication connection between the information terminal 200 and the portable terminal 300. For example, the information terminal 200 displays on the touch panel a communication end button to disconnect the communication connection. By pressing the communication end button displayed on the touch panel of the information terminal 200, the operator cuts off the communication connection between the information terminal 200 and the portable terminal 300.

Returning to the description FIG. 3, the security processing function 257 performs a virus check on the information terminal 200. For example, on the basis of a virus definition file, the security processing function 257 performs the virus check on the information terminal 200 that has ended the communication connection to the portable terminal 300. In this situation, when a virus is detected, the security processing function 257 removes the detected virus.

When the virus check by the security processing function 257 is completed, the communication connection to the ultrasound diagnosis apparatus 100 is re-established as a result of the controlling function 251 transmitting a request for a communication connection to the ultrasound diagnosis apparatus 100.

As explained above, in the ultrasound diagnosis system 1, the subject is able to arrange the image data to be transferred to the portable terminal 300 of his/her own, by simply reading the two-dimensional code twice on the portable terminal 300 of his/her own. It is therefore possible to conveniently provide the subject with the image data. Further, in the ultrasound diagnosis system 1, to transfer the image data, the communication line using the virtual access point is constructed, and the image data is transferred by using the constructed communication line. As a result, the operator is able to obtain the desired image data without being burdened with the communication fee for downloading a dedicated application.

Further, in the ultrasound diagnosis system 1, when the information terminal 200 is communicably connected to the portable terminal 300, the communication connection between the information terminal 200 and the ultrasound diagnosis apparatus 100 is cut off. As a result, it is possible provide the portable terminal 300 with the image data in a secure manner.

Figure 7:
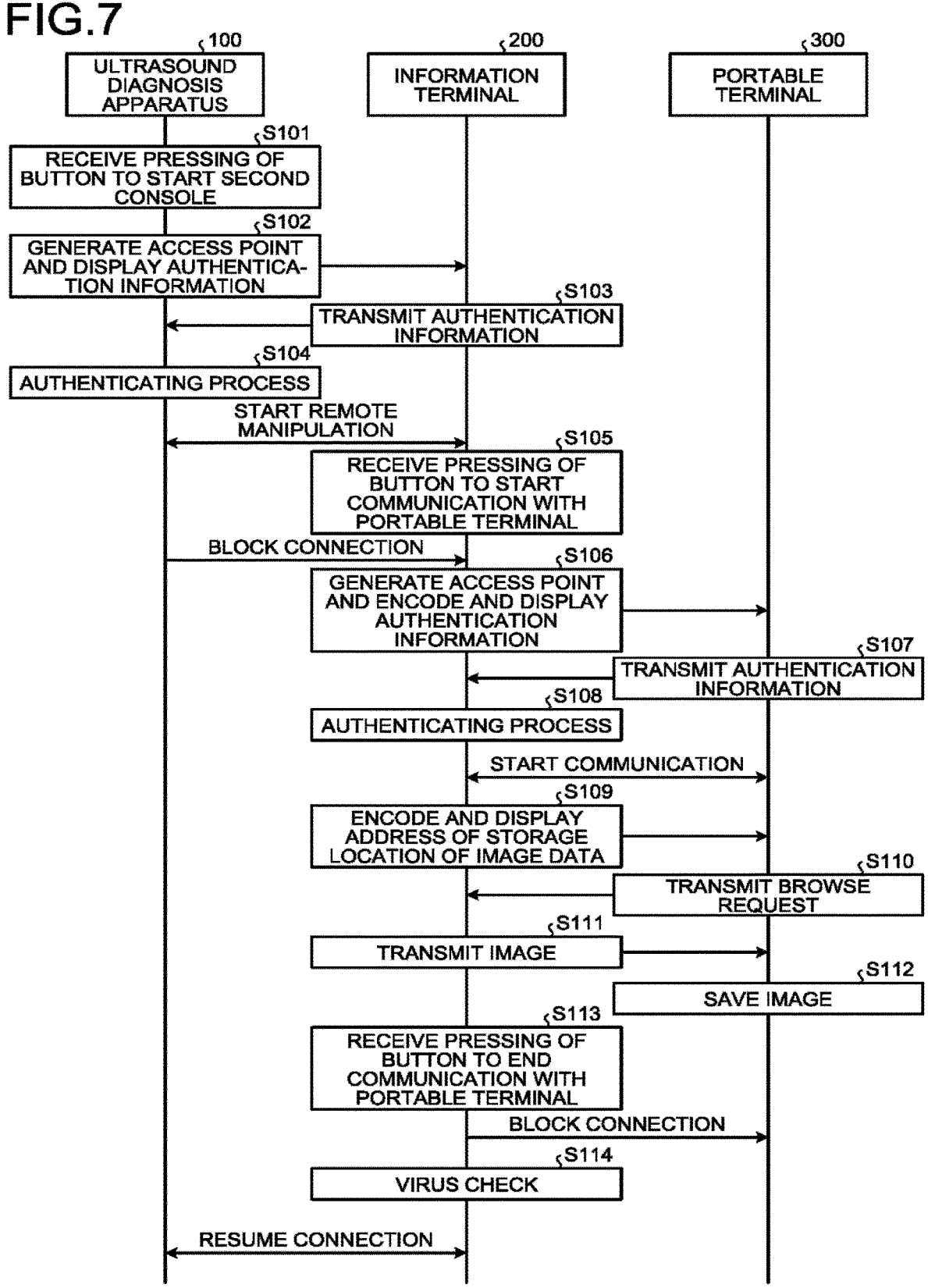
FIG. 7 is a sequence chart illustrating a flow in a process performed in the ultrasound diagnosis system according to the first embodiment.

Next, a flow in a process performed in the ultrasound diagnosis system 1 according to the first embodiment will be explained. FIG. 7 is a sequence chart illustrating the flow in the process performed in the ultrasound diagnosis system 1 according to the first embodiment. FIG. 7 illustrates an example in which a second console is applied to the ultrasound diagnosis system 1.

As illustrated in FIG. 7, in the ultrasound diagnosis system 1, when the ultrasound diagnosis apparatus 100 receives pressing of a second console start button to start the second console (step S101), the ultrasound diagnosis apparatus 100 generates a virtual access point so as to establish a communication connection to the information terminal 200, and displays authentication information (step S102). Further, the ultrasound diagnosis apparatus 100 transmits, to the information terminal 200, a request to input the authentication information for manipulating the ultrasound diagnosis apparatus 100 through the information terminal 200.

When having received the authentication information input request, the information terminal 200 transmits the authentication information to the ultrasound diagnosis apparatus 100, by receiving an input of the authentication information displayed on the ultrasound diagnosis apparatus 100 (step S103). When having received the authentication information from the information terminal 200, the ultrasound diagnosis apparatus 100 performs an authenticating process by comparing the received authentication information with the displayed authentication information (step S104). When the two pieces of authentication information match in the authenticating process, a remote manipulation of the ultrasound diagnosis apparatus 100 through the information terminal 200 is started in the ultrasound diagnosis system 1.

After that, when the information terminal 200 receives pressing of the button to start the communication with the portable terminal 300 (step S105), the information terminal 200 blocks the communication connection to the ultrasound diagnosis apparatus 100, generates a virtual access point, and encodes and displays the authentication information (step S106). The portable terminal 300 obtains the authentication information by reading the encoded authentication information and transmits the obtained authentication information to the information terminal 200 (step S107).

When having received the authentication information from the portable terminal 300, the information terminal 200 performs an authenticating process by comparing the received authentication information with the encoded authentication information (step S106). When the two pieces of authentication information match in the authenticating process, a communication connection between the information terminal 200 and the portable terminal 300 is started in the ultrasound diagnosis system 1.

Further, the information terminal 200 encodes and displays the address of the storage location of the image data to be transferred (step S109). The portable terminal 300 obtains the address of the image data by reading the encoded address and transmits a request to browse the obtained address to the information terminal 200 (step S110). When having received the browse request from the portable terminal 300, the information terminal 200 transmits the image corresponding to the request (the data stored at the address) to the portable terminal 300 (step S111).

When having received the image from the information terminal 200, the portable terminal 300 receives an operation from the subject and saves the image therein (step S112). After that, when the information terminal 200 receives pressing of the communication end button to end the communication with the portable terminal 300 (step S113), the information terminal 200 blocks the connection to the portable terminal 300 and performs a virus check (step S114). After the virus check, the information terminal 200 resumes the communication connection to the ultrasound diagnosis apparatus 100.

Figure 8:
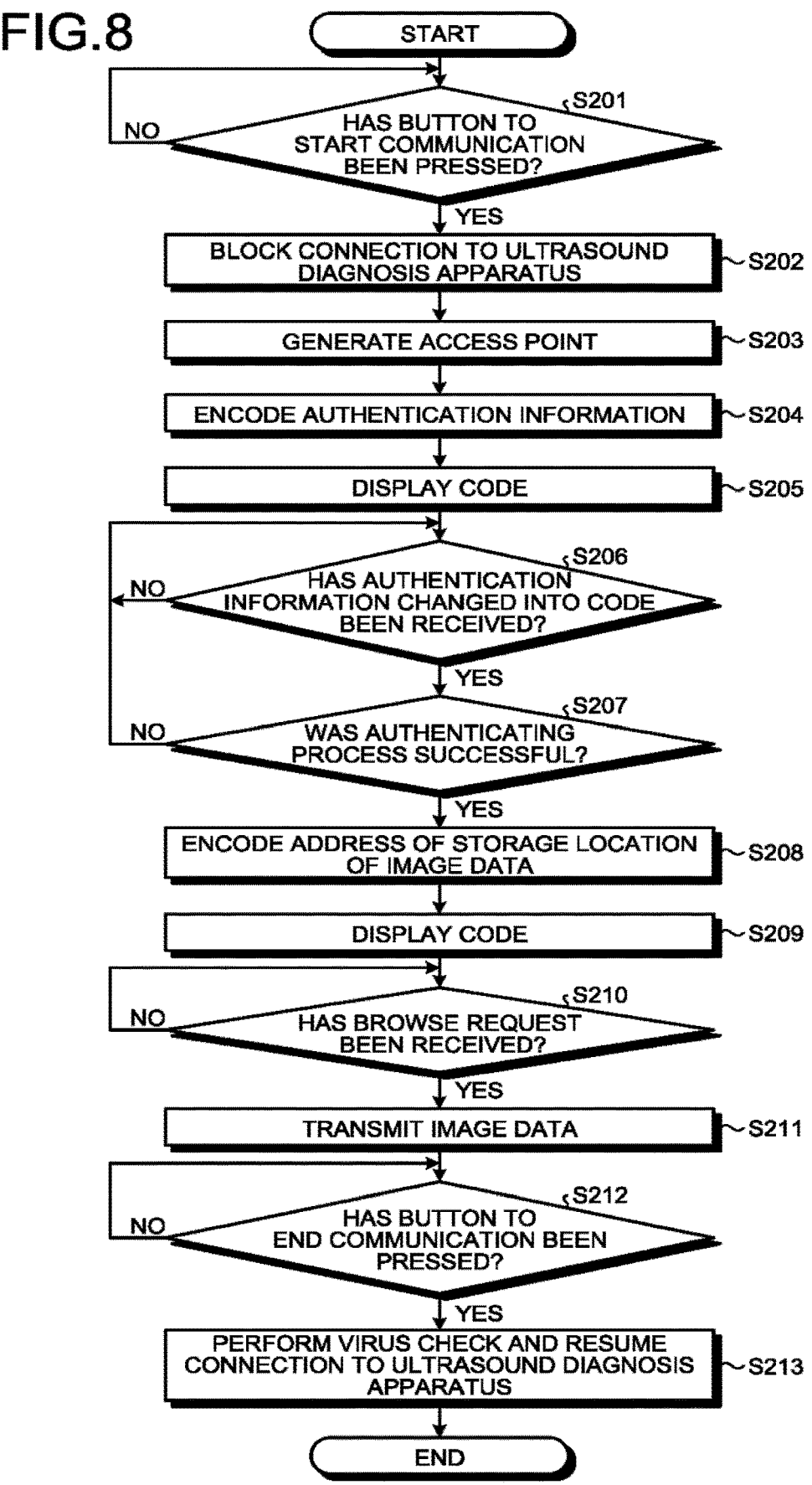
FIG. 8 is a flowchart illustrating a processing procedure performed by the information terminal according to the first embodiment.

Next, a procedure in a process performed by the information terminal 200 according to the first embodiment will be explained. FIG. 8 is a flowchart illustrating a processing procedure performed by the information terminal 200 according to the first embodiment. FIG. 8 illustrates the process performed by the information terminal 200 after a communication connection to the ultrasound diagnosis apparatus 100 is established.

Steps S201, S202, S205, S209, and S212 in FIG. 8 are realized as a result of, for example, the processing circuitry 25 reading and executing the program corresponding to the controlling function 251 from the memory 22. Step S203 is realized as a result of, for example, the processing circuitry 25 reading and executing the program corresponding to the access point function 253 from the memory 22. Step S204 is realized as a result of, for example, the processing circuitry 25 reading and executing the program corresponding to the encoding function 255 from the memory 22. Steps S206 and S207 are realized as a result of, for example, the processing circuitry 25 reading and executing the program corresponding to the authenticating function 256 from the memory 22. Step S208 is realized as a result of, for example, the processing circuitry 25 reading and executing the program corresponding to the image processing function 252 and the program corresponding to the encoding function 255 from the memory 22. Steps S210 and S211 are realized as a result of, for example, the processing circuitry 25 reading and executing the program corresponding to the server function 254 from the memory 22. Step S213 is realized as a result of, for example, the processing circuitry 25 reading and executing the program corresponding to the security processing function 257 from the memory 22.

As illustrated in FIG. 8, in the information terminal 200 according to the present embodiment, the processing circuitry 25 judges whether or not the button to start the communication with the portable terminal 300 has been pressed (step S201). When the subject presses the button (step S201: Yes), the processing circuitry 25 blocks the communication connection to the ultrasound diagnosis apparatus 100 (step S202) and generates an access point (step S203). Until the button to start the communication with the portable terminal 300 is pressed (step S201: No), the information terminal 200 keeps the communication connection to the ultrasound diagnosis apparatus 100.

Further, the processing circuitry 25 encodes the authentication information including the SSID of the access point and a password (step S204), causes the display 24 to display the code obtained from the encoding process (step S205), and judges whether or not the authentication information changed into a code has been received (step S206). When the authentication information is received (step S206: Yes), the processing circuitry 25 further judges whether the authenticating process is successful or not (step S207).

When the authenticating process using the received authentication information is successful (step S207: Yes), the processing circuitry 25 encodes the address of the storage location of the image data in which personal information is anonymized (step S208) and causes the display 24 to display the code obtained from the encoding process (step S209).

After that, the processing circuitry 25 judges whether or not a browse request for the encoded address has been received (step S210). When the browse request is received (step S210: Yes), the processing circuitry 25 transmits the image data corresponding to the received address to the portable terminal 300 (step S211) and judges whether or not the communication end button has been pressed (step S212). Subsequently, when the communication end button is pressed (step S212: Yes), the processing circuitry 25 performs a virus check on the information terminal 200 and resumes the communication connection to the ultrasound diagnosis apparatus 100 (step S213).

As explained above, in the ultrasound diagnosis system 1 according to the first embodiment, the ultrasound diagnosis apparatus 100 is configured to obtain the ultrasound image. The information terminal 200 connected to the ultrasound diagnosis apparatus 100 stores therein the ultrasound image transferred thereto from the ultrasound diagnosis apparatus 100, has the access point function, and displays a first code containing the identification information of the access point. Further, the information terminal 200 connects via the network to the portable terminal 300 that has read the first code and transfers the stored ultrasound image to the portable terminal 300 via the network. Accordingly, the ultrasound diagnosis system 1 according to the first embodiment makes it possible to conveniently provide the portable terminal 300 with the image data obtained by the ultrasound diagnosis apparatus 100.

Further, according to the first embodiment, the first code contains the password corresponding to the identification information. Accordingly, the ultrasound diagnosis system 1 according to the first embodiment is able to save the trouble of inputting the password for the subject who owns the portable terminal 300 and thus makes it possible to provide the image more conveniently.

Further, according to the first embodiment, the information terminal 200 is configured to display a second code containing the information about the storage location of the ultrasound image and, when the portable terminal 300 reads the second code, the information terminal 200 is configured to transfer the stored ultrasound image to the portable terminal 300 via the network. Consequently, the ultrasound diagnosis system 1 according to the first embodiment is able to save the trouble of inputting the information about the storage location of the image data for the subject who owns the portable terminal 300 and thus makes it possible to provide the image data more conveniently.

Further, according to the first embodiment, either the ultrasound diagnosis apparatus 100 or the information terminal 200 invalidates the connection between the ultrasound diagnosis apparatus 100 and the information terminal 200 before the information terminal 200 and the portable terminal 300 are connected to each other via the network. Consequently, the ultrasound diagnosis system 1 according to the first embodiment is able to avoid the situation where the portable terminal 300 owned by the subject is connected to the ultrasound diagnosis apparatus 100 or to the intra-hospital LAN and thus make it possible to realize the transfer of the image data in a secure state.

Further, according to the first embodiment, the information terminal 200 performs the virus scan, at a time that is after the information terminal 200 is connected to the portable terminal 300 via the network but is before the information terminal 200 is re-connected to the ultrasound diagnosis apparatus 100. Consequently, even if a virus enters the information terminal 200 from the portable terminal 300, the ultrasound diagnosis system 1 according to the first embodiment makes it possible to avoid the situation where the virus enters the ultrasound diagnosis apparatus 100 or other apparatuses connected to the intra-hospital LAN.

Further, according to the first embodiment, the information terminal 200 transfers the ultrasound image to the portable terminal 300 while the ultrasound image is in the anonymised state. Consequently, the ultrasound diagnosis system 1 according to the first embodiment makes it possible to prevent the personal information from leaking to the outside.

Further, according to the first embodiment, the password corresponding to the identification information and the information about the storage location of the ultrasound image are changed every time the portable terminal 300 is connected to the information terminal 200. Consequently, the ultrasound diagnosis system 1 according to the first embodiment makes it possible to provide the image data in a more secure manner.

Second Embodiment

The first embodiment has thus been explained. It is possible to carry out the present disclosure in various different modes other than those described in the first embodiment.

In the embodiments above, the example is explained in which only the ultrasound image is transferred to the portable terminal 300. However, possible embodiments are not limited to this example. An ultrasound image to which various types of information are added may be transferred. More specifically, the information terminal 200 stores therein image data obtained by adding information to an ultrasound image and transfers the stored image data to the portable terminal 300. For example, the information terminal 200 is able to transmit, to the portable terminal 300, image data indicating screen data displayed on the information terminal 200 and an ultrasound image. In another example, the information terminal 200 is able to transfer, to the portable terminal 300, image data having appended thereto a pictogram or a body mark that was appended to the ultrasound image by the information terminal 200. In that situation, the image processing function 252 generates the image data described above.

Figure 9:
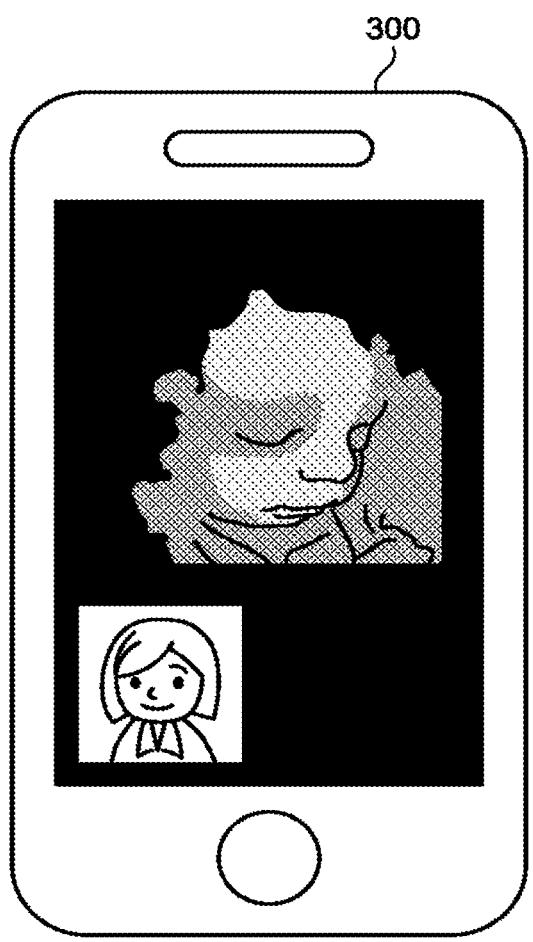
FIG. 9 is a drawing illustrating an example of image data according to a second embodiment.

Further, the information terminal 200 is also capable of transferring image data to which information is further added at the time of transferring the image data. For example, the information terminal 200 is capable of transferring, to the portable terminal 300, image data obtained by combining an ultrasound image with an image taken by a camera provided in the information terminal 200. FIG. 9 is a drawing illustrating an example of image data according to a second embodiment. For example, as illustrated in FIG. 9, the information terminal 200 is capable of transmitting, to the portable terminal 300, image data obtained by combining an ultrasound image of a fetus with a photo of the mother's face. In that situation, at first, the operator operates the information terminal 200 to take the photo of the mother's face. After that, the image processing function 252 generates the image data by combining the photo taken of the mother's face with the ultrasound image. In this situation, for example, the image processing function 252 combines the photo of the mother's face in such a position that does not overlap with the region of the fetus in the ultrasound image. As explained above, in the ultrasound diagnosis system 1 according to the second embodiment, it is possible to transfer the image data obtained by adding information to the ultrasound image. Consequently, the ultrasound diagnosis system 1 makes it possible to provide various types of information for the portable terminal 300.

Further, in the above embodiments, the example is explained in which the ultrasound diagnosis system 1 is applied to the obstetric checkup. However, possible embodiments are not limited to this example. For instance, the present disclosure may be applied to a maintenance service of the ultrasound diagnosis system 1. In that situation, for example, the ultrasound diagnosis system 1 may be applied to a situation where image data indicating occurrence of a malfunction is transferred to a portable terminal owned by a sales person in charge who services the ultrasound diagnosis system 1.

Further, in the above embodiments, the example is explained in which the authenticating process is performed when the information terminal 200 and the portable terminal 300 are communicably connected to each other, and the transfer of the image data is permitted by the authenticating process. However, possible embodiments are not limited to this example. For instance, an authenticating process may further be performed when the image data is transferred. In other words, after being communicably connected to the portable terminal 300 that has read the code obtained by encoding the authentication information of the access point, the information terminal 200 may perform an authenticating process using a password and further transfer the image data to the portable terminal 300 permitted in the authenticating process.

In that situation, for example, when a browse request is received by the server function 254, the controlling function 251 causes the display 24 to display a one-time password. Only when the password matching the one-time password displayed on the display 24 is received from the portable terminal 300, the server function 254 transmits the image data corresponding to the browse request to the portable terminal 300. With this arrangement, the ultrasound diagnosis system 1 makes it possible to provide the image data in a more secure manner.

Further, in the embodiments above, the example is explained in which the second console is applied to the ultrasound diagnosis system 1. However, possible embodiments are not limited to this example. It is possible to apply the present disclosure to any system in which the ultrasound diagnosis apparatus 100 and an information terminal are communicably connected to each other.

Further, in the embodiments above, the example is explained in which the information terminal 200 invalidates (blocks) the communication connection between the ultrasound diagnosis apparatus 100 and the information terminal 200. However, possible embodiments are not limited to this example. For instance, the ultrasound diagnosis apparatus 100 may invalidate the communication connection. In that situation, the ultrasound diagnosis apparatus 100 invalidates the communication connection to the information terminal 200 when having received a notification from the information terminal 200 indicating that the button to start the communication connection to the portable terminal 300 is pressed.

Further, in the embodiments above, the example is explained in which the information terminal 200 transfers the image data. However, possible embodiments are not limited to this example. For instance, the ultrasound diagnosis apparatus may transfer the image data. In other words, the ultrasound diagnosis apparatus 100 obtains the ultrasound image, stores the ultrasound image therein, has an access point function, displays a code containing the identification information of the access point, connects via a network to the terminal having read the code, and transfers the stored ultrasound image to the portable terminal 300 via the network.

In that situation, the processing circuitry 150 included in the ultrasound diagnosis apparatus 100 executes the controlling function 251, the image processing function 252, the access point function 253, the server function 254, the encoding function 255, the authenticating function 256, and the security processing function 257. In this situation, when the ultrasound diagnosis apparatus 100 transfers the image data to the portable terminal 300, the communication connection of the ultrasound diagnosis apparatus 100 to the intra-hospital LAN is invalidated, and the communication connection to the intra-hospital LAN is re-established after the communication connection to the portable terminal 300 is blocked.

Further, in the embodiments above, the one example is explained in which the ultrasound diagnosis system 1 including the ultrasound diagnosis apparatus serves as the medical system. However, possible embodiments are not limited to this example. For instance, the medical information transfer method described above may be applied to systems such as Picture Archiving and Communication Systems (PACS), Hospital Information Systems (HIS), or Radiology Information Systems (RIS).

In that situation, for example, communication connections to the information terminal 200 and to the portable terminal 300 are made to transmit and receive image data and medical information such as a medical report held in the system, as a result of processing circuits included in the information processing apparatuses such as server apparatuses and workstations included in the abovementioned system performing the same processes as those performed by the processing circuitry 150 described above.

Further, for example, the medical information transfer method described above may be applied to a system that includes other modalities such as one or more X-ray Computed Tomography (CT) apparatuses and/or Magnetic Resonance Imaging (MRI) apparatuses. In that situation, for example, communication connections to the information terminal 200 and to the portable terminal 300 are made to transmit and receive medical information such as image data held in the modalities, as a result of processing circuits included in the console devices and the gantries included in the modalities performing the same processes as those performed by the processing circuitry 150 described above.

Further, in the embodiments above, the example is explained in which the image data is transferred from a medical apparatus such as the ultrasound diagnosis apparatus 100 to the information terminal, so that the image data is further transferred from the information terminal 200 to the portable terminal 300. However, possible embodiments are not limited to this example. For instance, another arrangement is also acceptable in which the image data or the medical information such as the medical report is transferred from the portable terminal 300 to the information terminal 200, so that the medical information is further transferred from the information terminal 200 to a medical apparatus.

With this arrangement, for example, the portable terminal 300 that has stored therein image data or a medical report to be handed over from one hospital to another when the subject is transferred to the different hospital or vital data obtained by the subject on a daily basis is able to transfer the image data or the medical information such as the medical report to a medical apparatus in the hospital via the information terminal 200 in a secure and easy manner. In one example, when the subject is transferred to the different hospital, the medical information is transferred to the portable terminal 300 of the subject from a medical apparatus at the original hospital by using the method described above. After that, the medical information is further transferred from the portable terminal 300 of the subject to a medical apparatus at the new hospital. In this situation, by using the transfer method of the present disclosure, it is possible to transfer the medical information in a secure and easy manner. In the following sections, the transfer of the medical information from the portable terminal 300 will be explained.

In that situation, for example, or the information terminal 200, when a button to receive the image data or the medical information such as the medical report from the portable terminal 300 is pressed, the access point function 253 generates an access point and sets an SSID and a password. Further, the encoding function 255 changes the set SSID and password into a two-dimensional code. After that, the controlling function 251 causes the display 24 to display the two-dimensional code.

The subject operates the portable terminal 300 of his/her own and reads the two-dimensional code displayed on the display 24 by using the camera. As a result, the portable terminal 300 obtains the SSID and the password of the virtual access point. When having obtained the SSID and the password, the portable terminal 300 makes a communication connection between the information terminal 200 and the portable terminal 300, by transmitting the obtained SSID and password, as well as authentication information such as a MAC address of the portable terminal 300 to the information terminal 200.

The authenticating function 256 performs an authenticating process on the authentication information received from the portable terminal 300. More specifically, the authenticating function 256 receives the authentication information from the portable terminal 300 via the communication interface 21. Further, the authenticating function 256 compares the password included in the received authentication information with the password changed into the two-dimensional code. When the password included in the authentication information matches the password changed into the two-dimensional code, the authenticating function 256 permits the communication connection between the portable terminal 300 and the information terminal 200. In this situation, when the communication connection of the portable terminal 300 to the information terminal 200 is permitted, the access point function 253 establishes the communication connection between the information terminal 200 and the portable terminal 300.

In this situation, as explained above, when the information terminal 200 and the portable terminal 300 are communicably connected to each other, the communication connection between the information terminal 200 and the medical apparatus is cut off. In other words, before the information terminal 200 and the portable terminal 300 are communicably connected to each other, either the medical apparatus or the information terminal 200 invalidates the communication connection between the information terminal 200 and the medical apparatus.

In response to an upload request from the portable terminal 300 requesting that the image data or the medical information such as the medical report be uploaded, the server function 254 returns a response. For example, the server function 254 functions as a web server and receives an HTTP request to browse the URL of an upload screen from a web browser of the portable terminal 300. Further, in response to the received HTTP request, the server function 254 returns an upload screen to the web browser of the portable terminal 300.

In one example, when the button to receive image data or medical information such as a medical report from the portable terminal 300 is pressed, the server function 254 at first notifies the encoding function 255 of the URL of the storage location of the upload screen. The encoding function 255 changes the URL provided in the notification into a two-dimensional code. Further, when the URL has been changed into the two-dimensional code by the encoding function 255, the controlling function 251 causes the display 24 to display the two-dimensional code.

The subject operates the portable terminal 300 of his/her own and reads the two-dimensional code displayed on the display 24 by using the camera. As a result, the portable terminal 300 obtains the URL of the upload screen. When having obtained the URL of the upload screen, the portable terminal 300 transmits an HTTP request to browse the URL obtained by the web browser to the information terminal 200. In response to the HTTP request received from the portable terminal 300, the server function 254 transfers the upload screen at the requested URL to the web browser of the portable terminal 300.

Further, when the upload screen is transferred thereto from the information terminal 200, the portable terminal 300 is able to have the upload screen displayed in the web browser, for example. In this situation, as a result of the subject performing an operation to upload image data or medical information such as a medical report stored in the portable terminal 300 onto the upload screen in the web browser, the portable terminal 300 is able to upload the medical information into the information terminal 200. The information terminal 200 stores all of the uploaded medical information into the memory 22.

When the upload of all of the medical information from the portable terminal 300 has been completed, the operator performs an operation to cut off the communication connection between the information terminal 200 and the portable terminal 300. For example, the information terminal 200 arranges a communication end button used for disconnecting the communication connection to be displayed on the touch panel. The operator cuts off the communication connection between the information terminal 200 and the portable terminal 300, by pressing the communication end button displayed on the touch panel of the information terminal 200.

After that, when a virus check by the security processing function 257 is completed, a communication connection to the medical apparatus is established as a result of the controlling function 251 transmitting a communication connection request to the medical apparatus. In this situation, the communication connection between the medical apparatus and the information terminal 200 is realized in the same manner as the communication connection between the ultrasound diagnosis apparatus 100 and the information terminal 200 described above.

When the communication connection between the medical apparatus and the information terminal 200 is established, an operator operates the medical apparatus to open the data of the subject. For example, the operator opens a screen used for registering information about the subject, an input screen for medical examination data, an electronic medical record, and the like. Further, when the operator performs, on the medical apparatus, an operation to obtain the image data or the medical information such as the medical report of the subject stored in the information terminal 200, the processing circuitry included in the medical apparatus transmits a medical information transfer request to the information terminal 200. When having received the medical information transfer request from the medical apparatus, the controlling function 251 of the information terminal 200 transmits either the medical information or the medical information having been compressed to the medical apparatus.

When having received the medical information from the information terminal 200, the processing circuitry included in the medical apparatus stores the received medical information into a memory thereof. In this situation, the processing circuitry included in the medical apparatus stores the medical information into the memory, so as to be kept in correspondence with an identifier or the like that uniquely identifies the subject.

Next, a flow in a process performed in the medical system according to the second embodiment will be explained. FIG. 10 is a sequence chart illustrating the flow in the process performed in the medical system according to the second embodiment. FIG. 10 illustrates the flow in the process performed in the medical system including a medical apparatus 400. In this situation, the medical apparatus 400 may be an information processing apparatus such as a server apparatus or a workstation or may be a modality such as the ultrasound diagnosis apparatus 100.

As illustrated in FIG. 10, in the medical system, when pressing of a button to start the communication with the portable terminal 300 is received (step S301), the information terminal 200 blocks the communication connection to the medical apparatus, generates a virtual access point, and encodes and displays the authentication information (step S302). The portable terminal 300 obtains the authentication information by reading the encoded authentication information and transmits the obtained authentication information to the information terminal 200 (step S303).

When having received the authentication information from the portable terminal 300, the information terminal 200 performs an authenticating process by comparing the received authentication information with the encoded authentication information (step S304). When the two pieces of authentication information match in the authenticating process, the communication connection between the information terminal 200 and the portable terminal 300 is started in the medical system.

When the communication connection is started, the information terminal 200 encodes and displays the address of the upload screen (step S305). The portable terminal 300 obtains the address of the upload screen by reading the encoded address and transmits a browse request for the obtained address to the information terminal 200. When having received the browse request from the portable terminal 300, the information terminal 200 transmits the upload screen corresponding to the request to the portable terminal 300.

When having received the upload screen from the information terminal 200, the portable terminal 300 receives an operation from the subject and transmits data such as the image data or the medical report to the information terminal 200 (step S306). The information terminal 200 saves therein all of the received data (medical information) (step S307). Further, when pressing of the communication end button to end the communication with the portable terminal 300 is received on the information terminal 200 (step S308), the information terminal 200 blocks the connection to the portable terminal 300 and performs a virus check (step S309).

After the virus check, when having received pressing of the communication start button (step S310), the medical apparatus 400 generates a virtual access point, establishes a communication connection to the information terminal 200, and displays authentication information (step S311). Further, the medical apparatus 400 transmits an authentication information input request to the information terminal 200.

When having received the authentication information input request, the information terminal 200 transmits authentication information to the medical apparatus 400 by receiving an input of the authentication information displayed on the medical apparatus 400 (step S312). When having received the authentication information from the information terminal 200, the medical apparatus 400 performs an authenticating process by comparing the received authentication information with the displayed authentication information (step S313). When the two pieces of authentication information match in the authenticating process, a communication connection between the information terminal 200 and the medical apparatus 400 is started in the medical system.

After that, in the medical apparatus 400, the data of the corresponding subject is opened (step S314), and a medical information transfer request is transmitted thereby. When having received the transfer request from the medical apparatus 400, the information terminal 200 transmits data such as the image data or the medical report to the medical apparatus 100 (step S315). The medical apparatus 400 saves therein all of the received data so as to be kept in correspondence with the data of the corresponding subject (step S316).

As explained above, according to the second embodiment, the information terminal 200 is configured to store the medical information transferred thereto from the portable terminal 300 into the memory 22 and to transfer the stored medical information to the medical apparatus 400. Accordingly, the medical system according to the second embodiment makes it possible to transfer the image data or the medical information such as the medical report stored in the portable terminal owned by the subject, to the medical apparatus 400 in the hospital, in a secure and easy manner.

In the embodiments above, the examples are explained in which the single processing circuit (the processing circuitry 25 and the processing circuitry 150) realizes the processing functions; however, possible embodiments are not limited to those examples. For instance, the processing circuitry 25 (and the processing circuitry 150) may be structured by combining together a plurality of independent processors, so that the processing functions are realized as a result of the processors executing the programs. Further, the processing functions of the processing circuitry 25 (and the processing circuitry 150) may be realized as being integrated into a single processing circuit or distributed among a plurality of processing circuits, as appropriate.

Further, the constituent elements of the apparatuses and the devices illustrated in the drawings in the above embodiments are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a Central Processing Unit (CPU) and a program that is analyzed and executed by the CPU or may be realized as hardware using wired logic.

Further, with regard to the processes explained in the embodiments above, it is acceptable to manually perform a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

The term "processor" used in the above explanation denotes, for example, a Central Processing Unit (CPU), a Graphics Processing Unit (GPU), or a circuit such as an Application Specific integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in the memory 22 and the memory 140. In this situation, instead of saving the programs in the memory 22 and the memory 140, it is also acceptable to directly incorporate the programs in the circuits of the processors. In that situation, the processors realize the functions thereof by reading and executing the programs incorporated in the circuits thereof. The processors in the present embodiments do not each necessarily have to be structured as a single circuit. It is also acceptable to structure one processor by combining together a plurality of independent circuits so as to realize the functions thereof. Further, it is also acceptable to integrate two or more of the constituent elements in any of the drawings into one processor so as to realize the functions thereof.

Further, the medical information transfer methods explained in the above embodiments may be realized by causing a computer such as a personal computer or a workstation to execute an medical information transfer program prepared in advance. The medical information transfer program may be provided as being incorporated in a Read Only Memory (ROM), a storage unit, or the like, in advance. Further, the medical information transfer program may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like in a file in such a format that is either installable or executable for the devices. Further, the medical information transfer program may be stored in a computer connected to a network such as the Internet, so as to be provided or distributed as being downloaded via the network. For example, the medical information transfer program is structured with modules including the functional units described above. In the actual hardware, as a result of a CPU reading and executing the program from a storage medium such as a ROM, the modules are loaded into a main storage device so as to be generated in the main storage device.

According to at least one aspect to the embodiments described above, it is possible to conveniently provide the medical information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical system comprising:
a medical apparatus configured to have medical data therein; and
a first terminal including processing circuitry configured to be communicably connected to the medical apparatus so as to be able to transmit and receive the medical data thereto and therefrom, to store the medical data transferred from the medical apparatus into a memory, to have a function of an access point, and to cause a display to display a first code containing identification information of the access point, wherein
the processing circuitry is communicably connected to a second terminal having read the first code so as to be able to transmit and receive medical data thereto and therefrom,
the processing circuitry is configured to cause, after the processing circuitry detects that the second terminal connects to a wireless network using the first code, the display to display a second code containing information about a storage location of the medical data,
when the second terminal has read the second code, the processing circuitry is configured to transfer the medical data stored in the memory to the second terminal while the first terminal isn't communicably connected to the medical apparatus,
the processing circuitry is configured to perform a virus scan at a time that is after being communicably connected to the second terminal, but is before being re-connected to the medical apparatus, and
wherein the first code and the second code are distinguishable.

2. The medical system according to claim 1, wherein the processing circuitry is configured to store medical data transferred from the second terminal into a memory and transfer the stored medical data to the medical apparatus.

3. The medical system according to claim 1, wherein, before the first terminal and the second terminal are communicably connected to each other, the processing circuitry is configured to invalidate a connection made via the first terminal between the medical apparatus and the second terminal.

4. The medical system according to claim 1, wherein, before the first terminal and the second terminal are communicably connected to each other, processing circuitry included in the medical apparatus is configured to invalidate a connection made via the first terminal between the medical apparatus and the second terminal.

5. The medical system according to claim 1, wherein the first code contains a password corresponding to the identification information.

6. The medical system according to claim 5, wherein the password corresponding to the identification information is changed every time the second terminal is connected to the first terminal.

7. The medical system according to claim 1, wherein the information about the storage location of the medical data is changed every time the second terminal is connected to the first terminal.

8. The medical system according to claim 1, wherein the second code is changed every time the medical data is transferred.

9. The medical system according to claim 1, wherein the processing circuitry is configured to transfer the medical data in an anonymized state to the second terminal.

10. The medical system according to claim 1, wherein after being communicably connected to the second terminal that has read the first code, the processing circuitry is configured to perform an authenticating process by using a password and transfer the medical data to the second terminal permitted in the authenticating process.

11. The medical system according to claim 1, wherein the medical data is a medical image.

12. The medical system according to claim 1, wherein the medical data is a medical report.

13. The medical system according to claim 11, wherein the processing circuitry is configured to store image data obtained by adding information to the medical image into a memory, and transfer the stored image data to the second terminal.

14. A medical system comprising:
a medical apparatus that includes processing circuitry configured to obtain medical data, to store the medical data into a memory, to have a function of an access point, to cause a display to display a first code containing identification information of the access point, and to be communicably connected to a terminal having read the first code so as to be able to transmit and receive medical data thereto and therefrom,
wherein the processing circuitry is configured to cause, after the processing circuitry detects that a second terminal connects to a wireless network using the first code, the display to display a second code containing information about a storage location of the medical data,
when the second terminal has read the second code, the processing circuitry is configured to transfer the medical data stored in the memory to the second terminal while a first terminal isn't communicably connected to the medical apparatus, the processing circuitry is configured to perform a virus scan at a time that is after being communicably connected to the second terminal, but is before being re-connected to the first terminal, and wherein the first code and the second code are distinguishable.

15. A medical data transfer method implemented by a first terminal connected to a medical apparatus having medical data therein, comprising:

having a function of an access point, and causing a display to display a first code containing identification information of the access point;

communicably connecting to a second terminal having read the first code so as to be able to transmit and receive medical data thereto and therefrom, and storing the medical data transferred from the medical apparatus into a memory;

after that the second terminal connects to a wireless network using the first code, causing the display to display a second code containing information about a storage location of the medical data;

when the second terminal has read the second code, transferring the medical data stored in the memory to the second terminal while the first terminal isn't communicably connected to the medical apparatus; and performing a virus scan at a time that is after being communicably connected to the second terminal, but is before being re-connected to the medical apparatus, wherein the first code and the second code are distinguishable.

16. A medical data transfer method implemented by a medical apparatus to transfer medical data, comprising:

obtaining the medical data;

storing the medical data;

having a function of an access point;

causing a display to display a code containing identification information of the access point;

communicably connecting to a first terminal having read the code so as to be able to transmit and receive medical data thereto and therefrom;

invalidating connection between the medical apparatus and the first terminal before the first terminal and a second terminal are connected to each other; and performing a virus scan at a time that is after being communicably connected to the second terminal, but is before being re-connected to the first terminal.

* * * * *